US011713455B2

(12) United States Patent
Peytavi et al.

(10) Patent No.: US 11,713,455 B2
(45) Date of Patent: Aug. 1, 2023

(54) ENHANCED SELECTION OF EFFICIENT TARGETED GENOME MANIPULATING AGENTS

(71) Applicant: AMMR Joint Venture, La Jolla, CA (US)

(72) Inventors: Regis Peytavi, Costa Mesa, CA (US); Kiana Aran, Pasadena, CA (US); Brett Goldsmith, San Diego, CA (US); Alexander Kane, Santa Cruz, CA (US)

(73) Assignee: Cardea Bio, Inc., San Diego, CA (US)

( * ) Notice: Subject to any disclaimer, the term of this patent is extended or adjusted under 35 U.S.C. 154(b) by 655 days.

(21) Appl. No.: 16/782,795

(22) Filed: Feb. 5, 2020

(65) Prior Publication Data

US 2020/0248173 A1 Aug. 6, 2020

Related U.S. Application Data

(60) Provisional application No. 62/883,887, filed on Aug. 7, 2019, provisional application No. 62/866,312, filed on Jun. 25, 2019, provisional application No. 62/801,555, filed on Feb. 5, 2019.

(51) Int. Cl.
| | |
|---|---|
| *C12N 15/10* | (2006.01) |
| *C12N 9/22* | (2006.01) |
| *C12N 15/11* | (2006.01) |
| *B01L 3/00* | (2006.01) |
| *G16B 50/30* | (2019.01) |

(52) U.S. Cl.
CPC ........ *C12N 15/1013* (2013.01); *B01L 3/5025* (2013.01); *B01L 3/502707* (2013.01); *B01L 3/502715* (2013.01); *B01L 3/502761* (2013.01); *C12N 9/22* (2013.01); *C12N 15/102* (2013.01); *C12N 15/111* (2013.01); *B01L 2200/027* (2013.01); *B01L 2200/0668* (2013.01); *B01L 2300/022* (2013.01); *B01L 2300/0636* (2013.01); *C12N 2310/20* (2017.05); *G16B 50/30* (2019.02)

(58) Field of Classification Search
CPC .... C12N 15/1013; C12N 9/22; C12N 15/102; C12N 15/111; C12N 2310/20; B01L 3/5025; B01L 3/502707; B01L 3/502715; B01L 3/502761; B01L 2200/027; B01L 2200/0668; B01L 2300/022; B01L 2300/0636; G16B 50/30
See application file for complete search history.

(56) References Cited

U.S. PATENT DOCUMENTS

| | | | |
|---|---|---|---|
| 6,801,644 | B1 | 10/2004 | Shibata et al. |
| 10,428,319 | B2 | 10/2019 | Steinberg et al. |
| 2013/0308842 | A1 | 11/2013 | Blanchard et al. |
| 2014/0051588 | A9 | 2/2014 | Drmanac et al. |
| 2018/0355380 | A1 | 12/2018 | Shuber et al. |
| 2019/0112643 | A1* | 4/2019 | Aran .......................... C12N 9/22 |
| 2019/0338308 | A1 | 11/2019 | Sontheimer et al. |

FOREIGN PATENT DOCUMENTS

| | | |
|---|---|---|
| WO | 2018/097657 A1 | 5/2018 |
| WO | 2018097657 A1 | 5/2018 |

OTHER PUBLICATIONS

R.Hajian et al., "Detection of unamplified target genes via CRISPR-Cas9 immobilized on a graphene field-effect transistor", Nat Biomed Eng. Author manuscript; available in PMC, Dec. 1, 2019, pp. 1-24.
BR Goldsmith et al., "Digital Biosensing by Foundry-Fabricated Graphene Sensors", Scientific Reports, Jan. 22, 2019, pp. 1-10.
T. Bruegmann et al., "Evaluating the Efficiency of gRNAs in CRISP Mediated Genome Editing in Poplars", International Journal of Molecular Sciences, Jul. 24, 2019, pp. 1-19.
D. Carroll, "Genome Engineering With Zinc-Finger Nucleases", Genetics, vol. 188, Aug. 2011, pp. 773-782.
P. Akcakaya et al., "In vivo CRISPR editing with no detectable genome-wide off-target mutations", Nature. Sep. 2018; 561(7723): 416-419. doi:10.1038/s41586-018-0500-9., Sep. 2018, pp. 1-27.
G. Silva et al., "Meganucleases and Other Tools for Targeted Genome Engineering: Perspectives and Challenges for Gene Therapy", Current Gene Therapy vol. 11, No. 1, 2011, pp. 11-27.
XH Zhang et al., "Off-target Effects in CRISPR/Cas9-mediated Genome Engineering", Citation: Molecular Therapy—Nucleic Acids (2015) 4, e264; doi:10.1038/mtna.2015.37, Nov. 17, 2015, pp. 1-8.
C. Sanders, "*Preemptive Use Of Post-Grant Review* Vs. *Inter Partes Review*", Law 360, May 5, 2017, pp. 1-5.
M. Kosicki, "Repair of double-strand breaks induced by CRISPR-Cas9 leads to large deletions and complex rearrangements", Nat Biotechnol, Sep. 2018, pp. 1-16.

(Continued)

*Primary Examiner* — David C Thomas
(74) *Attorney, Agent, or Firm* — Kunzler Bean & Adamson

(57) ABSTRACT

For enhanced selection of efficient targeted genome manipulating agents, an apparatus includes first and second chip-based biosensors having one or more sensing surfaces configured to detect biomolecular binding interactions between a nucleic acid sample and a targeted genome manipulating agent functionalized to a capture surface within a sensing range of the one or more sensing surfaces. The first chip-based biosensor uses a nucleic acid sample incubated with a blocking agent that blocks on-target binding and the second chip-based biosensor holds a nucleic acid sample that omits the blocking agent. A measurement apparatus measures first and second sets of response signals produced in response to the biomolecular binding interactions occurring between the nucleic acid sample and the targeted genome manipulating agent. An analysis module determines the genome manipulating efficiency parameters of the targeted genome manipulating agent. A system and a method perform the functions of the apparatus.

16 Claims, 13 Drawing Sheets

(56) References Cited

OTHER PUBLICATIONS

JK. Joung et al., "TALENs: a widely applicable technology for targeted genome editing", Nat Rev Mol Cell Biol., Jan. 2013, pp. 1-16.

L. Shao et al., "Targeted gene disruption by use of a group II intron (targetron) vector in Clostridium acetobutylicum", Cell Research, Nov. 6, 2007, pp. 963-965.

S. Li et al., "CRISPR-Cas 12a-assisted nucleic acid detection", Cell Discovery vol. 4 No. 1, Apr. 24, 2018, pp. 1-4.

"Extended European Search Report", European Patent Office, dated Jul. 25, 2022, pp. 1-10.

C. Zheng et al., "Fabrication of ultrasensitive Field-Effect Transistor DNA Biosensors by a Directional Transfer Technique Based on CVD-Grown Graphene", Applied Materials & Interfaces vol. 7 No. 31, Jul. 30, 2015, pp. 16953-16959.

D. Reddy et al., "Graphene field-effect transistors", Journal of Physics D: Applied Physics vol. 44 No. 31, Jul. 14, 2011, pp. 16953-16959.

J.S. Gootenberg et al. "Nucleic acid detection with CROSPR-Cas13a/C2c2", Science vol. 356 No. 6336, Apr. 28, 2017, pp. 438-442.

PCT/US2020/016829, "Notification of Transmittal of the International Search Report and the Written Opinion of the International Searching Authority, or the Declaration", International Searching Authority, dated Jun. 19, 2020, pp. 1-25.

D. Singh et al., "Mechanisms of improved specificity of engineered Cas9s revealed by single-molecule FRET analysis", Nature Structural & Molecular Biology, vol. 25, Apr. 2018, pp. 347-354.

M.R. O'Connell et al., "Programmable RNA recognition and cleavage by CRISPR/Cas9", Nature, vol. 516, Dec. 11, 2014, pp. 1-14.

PCT/US2020/016829, "Invitation to Pay Additional Fees and, Where Applicable Protest Fee", International Searching Authority, dated Apr. 21, 2020, pp. 1-3.

B. Koo et al., "CRISPR/dCas9-mediated biosensor for detection of tick-borne disease", Sensors & Actuators: B. Chemical 271, Jun. 15, 2018, pp. 316-321.

R. Hajian et al., "Detection of unamplified target genes via CRISPR-Cas9 immobilized on a graphene field-effect transistor" Nat Biomed Eng. Jun. 2019 ; 3(6): pp. 427-437.

T. Bruegmann et al., "Evaluating the Efficiency of gRNAs in CRISPR/Cas9 Mediated Genome Editing in Poplars", International Journal of Molecular Sciences, Jul. 24, 2019, pp. 1-19.

D. Carroll, "Genome Engineering With Zinc-Finger Nucleases", Department of Biochemistry, Genetics Society of America, vol. 188, Aug. 2011, pp. 773-782.

G. Silva et al., "Meganucleases and Other Tools for Targeted Genome Engineering: Perspectives and Challenges for Gene Therapy", Current Gene Therapy, 2011, vol. 11, No. 1, pp. 11-27.

X. Zhang et al., "Off-target Effects in CRISPR/Cas9-mediated Genome Engineering", Citation: Molecular Therapy—Nucleic Acids vol. 4, Nov. 17, 2015, pp. 1-8.

C. Sanders et al., "*Preemptive Use Of Post-Grant Review* Vs. *Inter Partes Review*", Law360, May 5, 2017, pp. 1-5.

M. Kosicki et al., "Repair of double-strand breaks induced by CRISPR-Cas9 leads to large deletions and complex rearrangements", Nat Biotechnol, Sep. 2018, pp. 1-16.

\* cited by examiner

ENHANCED SELECTION OF EFFICIENT TARGETED GENOME MANIPULATING AGENTS

CROSS-REFERENCE TO RELATED APPLICATIONS

This application claims priority to U.S. Provisional Patent Application No. 62/801,555 entitled "Systems and Methods for Chip-Assisted CRISPR" filed Feb. 5, 2019, U.S. Provisional Patent Application No. 62/866,312 entitled "Systems and Methods for Electronic Detection of Cleavage and Collateral Activity of CRISPR-Associated Endonucleases" filed Jun. 25, 2019, and U.S. Provisional Patent Application No. 62/883,887 entitled "Devices and Methods for Label-free Detection of Analytes" filed Aug. 7, 2019, all of which are hereby incorporated by reference in their entireties to the extent legally allowable.

FIELD

The subject matter disclosed herein relates to biosensor systems and assays and more particularly relates to apparatuses, methods, computer program products, and systems for enhanced selection of efficient targeted genome manipulating agents.

BACKGROUND

Targeted genome manipulating has become a very potent tool in biology and medicine. For example, some targeted genome manipulating technologies perform gene editing to produce a double-strand break ("DSB") at a precise place in a genome, knocking out a specific gene by introducing indels at the DSB by the DNA repair machinery of a cell. When co-transfected with a vector producing a copy of a specific DNA sequence, targeted genome manipulating technologies can introduce a new DNA sequence at the DSB thus allowing, for example, replacement of an altered or dysfunctional gene with a working copy. Various screening and validation tools for genome manipulating targeting components include in vitro, in vivo, and in silico (e.g., computer-simulation) methods.

BRIEF SUMMARY

One general aspect includes an a first chip-based biosensor and a second chip-based biosensor, that individually may include one or more sensing surfaces configured to detect biomolecular binding interactions between a nucleic acid sample and one or more capture surfaces functionalized with a targeted genome manipulating agent having a genome manipulating component and a targeting component, where the one or more capture surfaces are within a sensing range of the one or more sensing surfaces, and where the first chip-based biosensor is configured to hold a first aliquot of the nucleic acid sample optionally incubated with a blocking agent configured to bind to a sequence overlapping an on-target sequence of the nucleic acid sample, and the second chip-based biosensor is configured to hold a second aliquot of the nucleic acid sample that omits the blocking agent. The apparatus also includes a measurement controller configured to measure one or more first and second response signals produced in response to the biomolecular binding interactions occurring between the nucleic acid sample in the first and second aliquots and the targeted genome manipulating agent on the functionalized capture surfaces of the first and second chip-based biosensors. The apparatus also includes an analysis module configured to determine one or more genome manipulating efficiency parameters associated with the targeted genome manipulating agent based on performing a comparison of the first and second response signals. Other embodiments of this aspect include corresponding computer systems, apparatus, and computer programs recorded on one or more computer storage devices, each configured to perform the actions of the methods.

One general aspect includes preparing a first aliquot and a second aliquot individually may include a nucleic acid sample where: the nucleic acid sample is to be measured for detecting biomolecular binding interactions between the nucleic acid sample dispensed to one or more sensing surfaces and a targeted genome manipulating agent that has a genome manipulating component and a targeting component and is functionalized to a capture surface within a sensing range of the one or more sensing surfaces, the first aliquot is optionally incubated with a blocking agent configured to bind to a sequence that overlaps an on-target sequence of the nucleic acid sample and the second aliquot omits the blocking agent. The method also includes measuring one or more first and second response signals produced in response to the biomolecular binding interactions occurring between the nucleic acid sample in the first and second aliquots, and the targeted genome manipulating agent on the functionalized capture surfaces of the first and second chip-based biosensors; and determining an efficiency parameter of the targeted genome manipulating agent based on comparing the one or more first response signals with the one or more second response signals. Other embodiments of this aspect include corresponding computer systems, apparatus, and computer programs recorded on one or more computer storage devices, each configured to perform the actions of the methods.

One general aspect includes a computer program product may include a computer readable storage medium having program instructions embodied therewith control the measurement of one or more first and second response signals produced by a first chip-based biosensor and a second chip-based biosensor, in response to biomolecular binding interactions occurring between a nucleic acid sample and a targeted genome manipulating agent that has an manipulating component and a targeting component and is functionalized to a capture surface within a sensing range of one or more respective sensing surfaces of a first chip-based biosensor and a second chip-based biosensor, where: the first chip-based biosensor is configured to hold a first aliquot of the nucleic acid sample optionally incubated with a blocking agent configured to bind to a sequence overlapping an on-target sequence of the nucleic acid sample and the second chip-based biosensor is configured to hold a second aliquot of the nucleic acid sample that omits the blocking agent. The product may further cause the processor to determine one or more genome manipulating efficiency parameters associated with the targeted genome manipulating agent based on performing a comparison of the first and second response signals. Other embodiments of this aspect include corresponding computer systems, apparatus, and computer programs recorded on one or more computer storage devices, each configured to perform the actions of the methods.

BRIEF DESCRIPTION OF THE DRAWINGS

A more particular description of the embodiments briefly described above will be rendered by reference to specific embodiments that are illustrated in the appended drawings. Understanding that these drawings depict only some embodiments and are not, therefore, to be considered to be limiting of scope, the embodiments will be described and explained with additional specificity and detail through the use of the accompanying drawings, in which.

DETAILED DESCRIPTION

Figure 1:
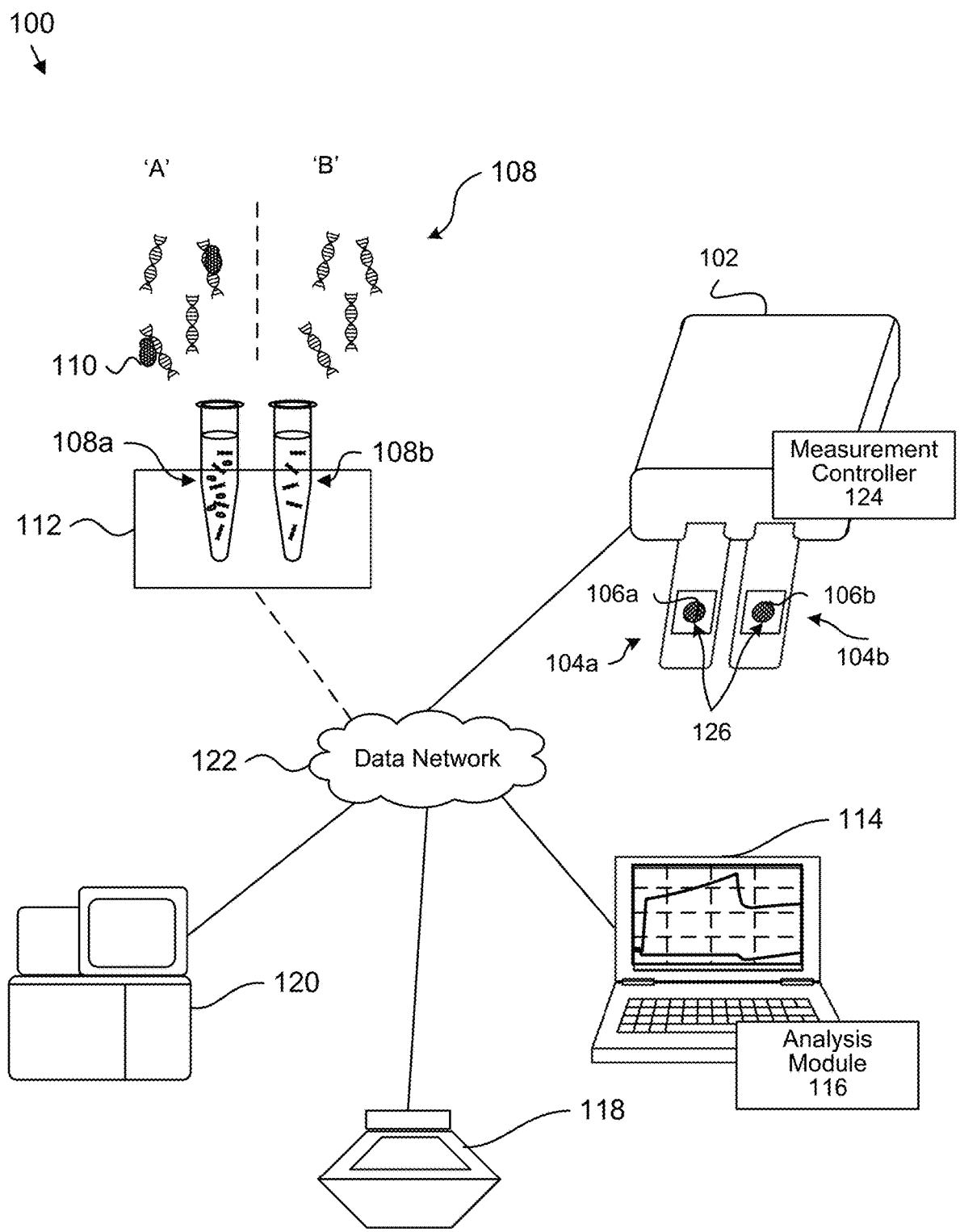
FIG. 1 is a schematic block diagram illustrating a system for enhanced selection of an efficient targeted genome manipulating agent, according to one or more aspects of the present disclosure.

As will be appreciated by one skilled in the art, aspects of the disclosure may be implemented as a system, method or program product. Accordingly, aspects or implementations may take the form of an entirely hardware implementation, an entirely software implementation (including firmware, resident software, micro-code, etc.) or an implementation combining software and hardware aspects that may all generally be referred to herein as a "circuit," "module," "controller," or "system." Furthermore, aspects of the disclosed subject matter may take the form of a program product implemented in one or more computer readable storage devices storing machine-readable code, computer readable code, and/or program code, referred hereafter as code. The storage devices may be tangible, non-transitory, and/or non-transmission. The storage devices may not embody signals. In a certain implementation, the storage devices only employ signals for accessing code.

Certain of the functional units described in this specification have been labeled as modules or controllers, in order to more particularly emphasize the implementation options that may be used. For example, some functions of a module or a controller may be implemented as a hardware circuit comprising custom VLSI circuits or gate arrays, off-the-shelf semiconductors such as logic chips, transistors, or other discrete components. A module or controller may also be implemented in programmable hardware devices such as field-programmable gate arrays, programmable array logic, programmable logic devices or the like.

Various modules or controllers may also be implemented in part or in whole, in code and/or software for execution by various types of processors. An identified controller or module of code may, for instance, comprise one or more physical or logical blocks of executable code which may, for instance, be organized as an object, procedure, or function. Nevertheless, the executables of an identified controller or module need not be physically located together but may comprise disparate instructions stored in different locations which, when joined logically together, comprise the module and achieve the stated purpose for the controller or module.

Indeed, a controller or a module of code may be a single instruction, or many instructions, and may even be distributed over several different code segments, among different programs, and across several memory devices. Similarly, operational data may be identified and illustrated herein within modules and may be embodied in any suitable form and organized within any suitable type of data structure. The operational data may be collected as a single data set or may be distributed over different locations including over different computer readable storage devices. Where a controller, module or portions thereof are implemented in software, the software portions are stored on one or more computer readable storage devices.

Any combination of one or more computer readable medium may be utilized. The computer readable medium may be a computer readable storage medium. The computer readable storage medium may be a storage device storing the code. The storage device may be, for example, but not limited to, an electronic, magnetic, optical, electromagnetic, infrared, holographic, micromechanical, or semiconductor system, apparatus, or device, or any suitable combination of the foregoing.

More specific examples (a non-exhaustive list) of the storage device would include the following: an electrical connection having one or more wires, a portable computer diskette, a hard disk, a random access memory (RAM), a read-only memory (ROM), an erasable programmable read-only memory (EPROM or Flash memory), a portable compact disc read-only memory (CD-ROM), an optical storage device, a magnetic storage device, or any suitable combination of the foregoing. In the context of this document, a computer readable storage medium may be any tangible medium that can contain or store a program for use by or in connection with an instruction execution system, apparatus, or device.

Code for carrying out operations for some implementations may be written in any combination of one or more programming languages including an object-oriented programming language such as Python, Ruby, Java, Smalltalk, C++, or the like, and conventional procedural programming languages, such as the "C" programming language, or the like, and/or machine languages such as assembly languages. The code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Reference throughout this specification to "one aspect," "an aspect," or similar language means that a particular feature, structure, or characteristic described in connection with the aspect is included in at least one implementation. Thus, appearances of the phrases "in one implementation," "in an implementation," and similar language throughout this specification may, but do not necessarily, all refer to the same implementation, but mean "one or more but not all implementations" unless expressly specified otherwise. The terms "including," "comprising," "having," and variations thereof mean "including but not limited to," unless expressly specified otherwise. An enumerated listing of items does not imply that any or all of the items are mutually exclusive unless expressly specified otherwise. The terms "a," "an," and "the" also refer to "one or more" unless expressly specified otherwise.

Furthermore, the described features, structures, or characteristics of the aspects or implementations may be combined in any suitable manner. In the following description, numerous specific details are provided, such as examples of programming, software modules, user selections, network transactions, database queries, database structures, hardware modules, hardware circuits, hardware chips, etc., to provide a thorough understanding of aspects and implementations. One skilled in the relevant art will recognize, however, that an implementation may be practiced without one or more of the specific details, or with other methods, components, materials, and so forth. In other instances, well-known structures, materials, or operations are not shown or described in detail to avoid obscuring aspects of the implementation.

Aspects of the disclosed implementations are described below with reference to schematic flowchart diagrams and/or schematic block diagrams of methods, apparatuses, systems, and program products according to examples. It will be understood that some blocks of the schematic flowchart diagrams and/or schematic block diagrams, and combinations of blocks in the schematic flowchart diagrams and/or schematic block diagrams, can be implemented by code. This code may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the schematic flowchart diagrams and/or schematic block diagrams block or blocks.

The schematic flowchart diagrams and/or schematic block diagrams in the Figures illustrate the architecture, functionality, and operation of possible implementations of apparatuses, systems, methods and program products according to various embodiments. In this regard, each block in the schematic flowchart diagrams and/or schematic block diagrams may represent a module, segment, or portion of code, which comprises one or more executable instructions of the code for implementing the specified logical function(s).

It should also be noted that, in some alternative implementations, the functions noted in the block may occur out of the order noted in the Figures. For example, two blocks shown in succession may, in fact, be executed substantially concurrently, or the blocks may sometimes be executed in the reverse order, depending upon the functionality involved. Other steps and methods may be conceived that are equivalent in function, logic, or effect to one or more blocks, or portions thereof, of the illustrated Figures.

Although various arrow types and line types may be employed in the flowchart and/or block diagrams, they are understood not to limit the scope of the corresponding aspects or implementations. Indeed, some arrows or other connectors may be used to indicate only the logical flow of the depicted example aspect. For instance, an arrow may indicate a waiting or monitoring period of unspecified duration between enumerated steps of the depicted example implementation. It will also be noted that each block of the block diagrams and/or flowchart diagrams, and combinations of blocks in the block diagrams and/or flowchart diagrams, can be implemented by special purpose hardware-based systems that perform the specified functions or acts, or combinations of special purpose hardware and code.

The description of elements in each figure may refer to elements of proceeding figures. Unless expressly noted or otherwise clear from context, like numbers refer to like elements in all figures, including alternate implementation involving like elements.

As used herein, a list using the conjunction of "and/or" includes any single item in the list or a combination of items in the list. For example, a list of A's, B and/or C includes only A, only B, only C, a combination of A and B, a combination of B and C, a combination of A and C or a combination of A, B and C. As used herein, a list using the terminology "one or more of" includes any single item in the list or a combination of items in the list. For example, one or more of A, B and C includes only A, only B, only C, a combination of A and B, a combination of B and C, a combination of A and C or a combination of A, B and C. As used herein, a list using the terminology "one of includes one and only one of any single items in the list. For example, "one of A, B and C" includes only A, only B or only C and excludes combinations of A, B and C. As used herein, "a member selected from the group consisting of A, B, and C," includes one and only one of A, B, or C, and excludes combinations of A, B, and C." As used herein, "a member selected from the group consisting of A, B, and C and combinations thereof" includes only A, only B, only C, a combination of A and B, a combination of B and C, a combination of A and C or a combination of A, B, and C.

The present disclosure describes various aspects and implementation of methods, systems, and apparatuses for enhanced selection of efficient targeted genome manipulating agents. Various examples of the described aspects address many of the drawbacks associated with existing methods for selecting targeted genome manipulating agents.

Definitions. The term "beads" as used herein, refers to particles in the range of about 1 nm to 10 μm in diameter having a functionalized surface configured to bind with a corresponding component of a molecule in solution. Some beads are magnetic and other beads are non-magnetic. Non-limiting examples of beads include particles functionalized with a streptavidin coating configured to bind with biotinylated molecules in solution. Other non-limiting examples of materials for functionalizing a bead surface include antibodies, streptavidin, neutravidin, avidin, captavidin, zinc finger protein, CRISPR Cas family enzymes, nucleic acids, and synthetic nucleic acid analogs such as peptide nucleic acid, xeno nucleic acid, and the like.

The term "binding" as used herein, refers to an electrostatic interaction between a genome manipulating agent and its nucleic acid target. Non-limiting examples include an interaction promoted by a protein-to-nucleic acid interaction, such as with TALEN or ZFN genome manipulating technology, or by a riboprotein complex such as CRISPR Cas9 and targetron.

The term "biology gated transistor" as used herein, refers to a transistor that is gated by changes in the surface potential induced by the binding of molecules.

The term "biomolecular" as used herein, refers to involving any molecule that is produced by a biological organism, including large polymeric molecules such as proteins, polysaccharides, lipids, and nucleic acids (DNA and RNA) as well as small molecules such as primary metabolites, secondary metabolites, and other natural products.

The term "chip-based biosensor" as used herein, refers a device comprising one or more solid two-dimensional sensor elements arranged on a solid support that respond directly or indirectly to the presence of a proximate biochemical or biomolecular analyte or interaction or both in a sample on or sufficiently proximate to produce an electrical or electromagnetic response signal suitable for amplification, filtering, digitization, and other analog and digital signal processing operations. Some "chip-based biosensors" comprise a plurality of transistors and a plurality of detection moieties where at least one of the transistors is a liquid gated transistor.

The terms "cleavage" or "cut" of nucleic acids, as used herein, refer to the breakage of the covalent backbone of a nucleic acid molecule. Cleavage can be initiated by a variety of methods including, but not limited to, enzymatic or chemical hydrolysis of a phosphodiester bond. With respect to DNA, the term "cleavage" or "cut" as used herein, refers to a double-stranded cleavage occurring as a result of two distinct single-stranded breakage events. DNA cleavage can result in the production of either blunt ends or staggered "sticky" ends.

The term "DNA recognition complex" as used herein, in the context of genome manipulating technology may refer to a protein, a naturally occurring or artificially develop nucleic acid, or a complex of nucleic acid and protein used to target a specific region, sequence, or site of a genome. Non-limiting examples of a DNA recognition complex may include in the context of CRISPR, a guide RNA and a Cas nuclease, such as Cas9, Cas13, or another engineered Cas nuclease active or mutated to prevent DSB. A DNA recognition complex for Transcription activator-like effector nuclease (TALEN), or other editing genome technologies using TAL (Transcription Activator-Like effector) such as TAL-Deaminase, where the DNA recognition complex is the transcription activator-like effector in combination with an active nuclease, such as Fok1, or a deaminase, or the TAL alone. Another example of a DNA recognition complex for Zing Finger Polymerase or (ZFP) is a complex made of small zing finger domains Cys2His2 combined with a type IIS non-specific DNA cleavage domain of the Fok1 restriction enzyme. Another example of a DNA recognition complex includes a targetron which is a ribonucleoprotein particle (RNP) having an engineered group II intron RNA lariat molecule and a multidomain group II intron-encoded protein. Recognition and cleavage are promoted by both the RNA lariat molecule which has ribozyme activity, and the Intron-Encode-protein that help for the recognition of the targeted sequence by stabilizing the RNA at its specific sequence and help the cleavage process and insertion of new DNA sequence by its reverse transcriptase activity.

The term "endonuclease" as used herein, refers to any wild-type or variant enzyme capable of catalyzing the hydrolysis (cleavage) of bonds between nucleic acids within a nucleic acid molecule such as DNA and/or RNA. Non-limiting examples of endonucleases include type II restriction endonucleases such as FoId, HhaI, HindIII, NotI, BbvCI, EcoRI, BglII, and AlwI. Non-limiting examples of endonucleases also include rare-cutting endonucleases when having typically a polynucleotide recognition site of about 12-45 base pairs (bp) in length, more preferably of 14-45 bp. Rare-cutting endonucleases induce DNA double-strand breaks (DSBs) at a defined locus. Rare-cutting endonucleases can, for example, be a homing endonuclease, a mega-nuclease, a chimeric Zinc-Finger nuclease (ZFN) or TAL effector nuclease (TALEN) resulting from the fusion of engineered zinc-finger domains or TAL effector domain, respectively, with the catalytic domain of a restriction enzyme such as Fok1, other nuclease or a chemical endonuclease. The endonuclease can be also part of the Cas family such as Cas9, Cas12, Cas13, and so forth.

The term "genome manipulating" as used herein, refers to something capable of modifying a component or behavior of a nucleic acid, gene, exon, nucleic acid sequence, genome, and/or similar nucleotide combination. Genome manipulating is not limited to manipulation of a whole genome or even to nucleic acid sequences found in a naturally occurring genome but may include any of the foregoing components whether artificially derived or naturally occurring. Non-limiting examples of genome manipulating include genome editing, chromatin engineering, chromatin imaging, epigenetic editing, gene activation, gene suppression, and so forth.

The term "off-target" as used herein, refers to at a region of a nucleic acid sample other than an intended or expected predetermined site (e.g., a targeted sequence) of the nucleic acid e.g., with respect to binding, cleavage, editing, manipulation, and/or other biomolecular interactions of the nucleic acid sample. The term "on-target" as used herein, refers to at a region of a nucleic acid sample corresponding to an intended or expected predetermined site (e.g., a targeted sequence) of the nucleic acid e.g., with respect to binding, cleavage editing, manipulation, and/or other biomolecular interactions of the nucleic acid sample. The term "on-plus-off-target" refers to the combination of both on-target and off-target biomolecular interactions.

The term "targeted genome manipulating agent" as used herein, refers to a biomolecular agent intended or expected to modify a component or a behavior of a nucleic acid, gene, exon, nucleic acid sequence, genome, and/or similar nucleotide combination at a predetermined site (e.g., a targeted sequence) of an intended or expected region, site, or sequence.

Although various genome manipulating technologies exist, the system, apparatuses, methods, and computer programs for enhanced selection of efficient targeted genome manipulating agents allows specific regions, genes, sites, sequences, and so forth, provide significant improvements over existing technologies. The benefits extend not only to the discovery of efficient targeting agents but also to improve the use of targeted genome manipulation agents. For example, with regard to genome editing, targeting the introduction of a non-mutated gene at a very precise place into the genome presents several advantages. First, it allows the added DNA sequence to be introduced in an area of the chromatin that is programmed to be precisely regulated for the expression of the said gene. Second, targeted genome editing also helps prevent dangerous random insertions that have been found to cause cancer in non-targeted gene therapy. Thus, by practicing the various aspects and implementations of the present disclosure, the efficiency of downstream technologies such as amplification, sequencing, and therapeutic uses of targeted genome manipulation agents may also be enhanced by allowing such downstream to be more efficiently utilized.

Other genome manipulating technologies do not produce double-strand breaks DSB but instead correct a single nucleotide polymorphism responsible for a deleterious gene. Such technologies usually use deaminase or other DNA repair enzymes to reverse the mutation into the wild type nucleotide base. Another category of targeted genome manipulating technology does not change the DNA but instead targets the epigenetic code driving the expression of the gene of importance.

Various aspects of targeted genome manipulating technologies differ in the way they repair the genetic code or modify the epigenetic code. Yet various genome manipulating technologies all use a system that targets the region or gene to be modified or affected. The systems, apparatuses, methods and computer programs for enhanced selection of efficient targeted genome manipulating agents utilize comparatively fast and inexpensive electronic biosensing systems, and thus improves the targeted genome manipulating technologies, for example, by increasing the precision of the targeting and reducing the cost and time for such screening and validation.

Various aspects of the systems, apparatuses, methods, and computer program products described herein may be used with different targeted genome manipulating systems. For example, with regard to targeted genome edit systems, a first group of specific DNA sequence targeting systems achieves specific DNA sequence targeting via protein interaction with DNA. Systems in the first group may include, for example, meganucleases ("MN"), zinc finger nucleases (ZFN) and transcription activator-like effector nucleases ("TALEN").

A second group of specific DNA sequence targeting systems achieves specific DNA sequence targeting via interactions between nucleic acids. Systems in the second group include for example targetron peptide nucleotide triplex-forming oligonucleotide ("TFO"s), structure-guided endonuclease ("SGN"), and Clustered Regularly Interspaced Short Palindromic Repeats ("CRISPR").

Although various aspects of the present disclosure may be utilized with any of the targeted technologies above, applying such aspects to the second group, and especially to CRISPR-Cas9, facilitates easy targeting of a desired sequence in a genome by changing just the sequence of the nucleic acid guiding modification enzymes or nucleases to their targets.

With existing technologies, designing a guide nucleic acid that provides an efficient target recognition without off-target site recognition is not readily achieved, especially for complex genomes such as a human genome. Additionally, the existence of off-target binding of a particular nucleic acid site to a targeted genome manipulation agent may create problems beyond the inefficient use of time and resources. For example, CRISPR-Cas9, one of the most successful genome-editing technologies, may exhibit a significant possibility of editing at an off-target site if the guide RNA ("gRNA") is not well-designed and tested. In turn, editing at an off-target site by CRISPR-Cas9 may result in nonspecific and/or unintended genetic modifications such as deleterious mutations and chromosomal aberrations.

Some existing tools and/or methods assess the on-site target efficiency and putative off-target site of CRISPR-associated gRNA but have deficiencies that may be solved by various aspects of the present disclosure. Such existing tools and/or methods may be classified into three groups: in silico, in vivo and in vitro methods.

In silico methods (e.g., computer simulations) may be used for a first high-level screening to eliminate gRNA that have a high probability of not working efficiently with an on-target site. However, existing in silico methods have not yet been able to demonstrate the ability to determine a gRNA that will work in real-world applications as predicted. Furthermore, existing in silico methods may be used to predict off-target putative recognition sites of a specific gRNA but lack the sensitivity and specificity required to make a reliable tool because in silico methods may miss certain important off-targeted putative sites (e.g., a false positive determination of an effective guide RNA) and may give a very high background of putative off-target sites that are not found in vivo (e.g., a false negative or rejection of a guide RNA that is effective in vivo).

In vitro methods, such as for example, Tracking of Indels by DEcomposition" ("TIDE"), Indel Detection by Amplicon Analysis ("IDAA"), and mismatch cleavage assays such as T7 Endonuclease I ("T7E1") or Surveyor nuclease, have been developed to assess gRNA cleavage efficiency. Yet, such methods require a transfection cell step, which makes them less user-friendly and more cumbersome than various of the systems, apparatuses, methods, and computer program products described herein which do not require a transfection cell step.

In vivo methods may be used for off-target putative site discovery. For example, some in vivo methods, such as Guide-Seq or Digenome-Seq are considered by some to be good predictive tools for assessing off-target sites for a given gRNA. However, such methods have disadvantages. For example, Guide-Seq requires efficient delivery of the double-stranded oligonucleotide, which may be toxic to some cell types at some doses and has not been demonstrated for in vivo models. In vivo methods are cumbersome, time-consuming, costly and more difficult to make reproducible. In vivo methods may also be influenced by cell fitness (e.g., may be sensitive to time of cell fixation) and may require the use of a relatively large number of cells and/or cells that are transfected or transduced.

Thus, certain in vitro methods that may be more convenient have been developed to overcome some of the limitations of in vivo methods. Some, examples of in vitro methods include Circle-Seq and Site-Seq which enrich putative CRISPR Cas9 off-targeted sites found in a whole-genome and then sequence them by Next Generation Sequencing ("NGS"). Although significant advances have been made over the past 20 years to reduce the average cost per human genome of NGS, in the past 5 years the steep decreases in NGS costs have significantly leveled off and such methods are still quite expensive to be used for screening for gRNA efficiency relative to the various genome biosensing system and method of this disclosure. Furthermore, a number of in vitro methods do not work well with chromatin, which is a determinant factor in assessing Cas9 activity in vivo. One method for assessing CRISPR-Cas9 off-target sites directly on chromatin is described in the abstract of WO2018097657 (A1). However, the method does not provide for enrichment of off-target putative sites and requires whole-genome sequencing to assess the off-target putative sites.

Accordingly, the various aspects of the present disclosure may be used also be used to enhance off-target putative site discovery using the chip-based biosensor systems and methods described below to provide much lower costs, faster screening and validation, and better precision for off-target site discovery. Certain chip-based biosensors such as biosensors that utilize field-effect biosensing provide for label-free measuring that is faster, can be manufactured at a lower cost, with higher repeatability and lower complexity than other measurement technologies that are not chip-based or that involve expensive fluidics and/or precision optical measuring devices.

FIG. 1 is a schematic block diagram illustrating a system 100 for enhanced selection of an efficient targeted genome manipulating agent, according to one or more aspects of the present disclosure. The system 100 in various implementations include one or more of a sample prep apparatus 112, a biomolecular measurement apparatus 102, a computing device 114, an enrichment apparatus 118, a sequencing apparatus 120, and a data network 122.

In at least one implementation, the biomolecular measurement apparatus 102 includes a first chip-based biosensor 104a and a second chip-based biosensor 104b. The biomolecular measurement apparatus also includes in various implementations, a measurement controller 124 configured to measure one or more first and second response signals produced in response to the biomolecular binding interactions occurring between the nucleic acid sample in the first and second aliquots and the targeted genome manipulating agent on the functionalized capture surfaces of first and second chip-based biosensors 104a, 104b. A first chip-based biosensor 104a and a second chip-based biosensor 104b. In certain implementations, each chip-based biosensor 104a, 104b has one or more sensing surfaces 106a, 106b configured to detect biomolecular binding interactions between nucleic acid sample 108 and one or more capture surfaces 126 within a sensing range of the one or more sensing surfaces 106a, 106b.

In FIG. 1, the chip-based biosensors 104a, 104b are depicted as separate from each other and removable from a chassis of the biomolecular measurement apparatus 102. In some implementations, the first chip-based biosensor 104a and the second chip-based biosensor 104b may be implemented, for example, so that the first, second, and/or more biosensors are supported by the same substrate. Similarly, the one or more sensing surfaces 106a, 106b may be arranged in various array configurations and may be configured alike or different. Furthermore, the first chip-based biosensor 104a and the second chip-based biosensor 104b may be implemented in a nonremovable configuration. In various implementations, the biomolecular measurement apparatus 102 includes a measurement controller 124 that is configured to measure one or more first and second response signals produced in response to the biomolecular binding interactions occurring between the nucleic acid sample in the first and second aliquots and the targeted genome manipulating agent on the functionalized capture surfaces of first and second chip-based biosensors.

In certain implementations, the first chip-based biosensor 104a is configured to hold a first aliquot 108a of the nucleic acid sample 108 that is optionally incubated with a blocking agent 110 configured to bind to a sequence overlapping an on-target sequence of the nucleic acid sample 108. In various implementations, the incubation with the blocking agent 110 is useful because it enables both the first chip-based biosensor 104a and the second chip-based biosensor 104b to utilize the same functionalized capture surfaces. In such implementations, the second chip-based biosensor 104b is configured to hold a second aliquot 108b of the nucleic acid sample 108 that omits the blocking agent 110.

Instead of using identically functionalized capture surfaces on both the first chip-based biosensor 104a and the second chip-based biosensor 104b, one of the chip-based biosensors may be functionalized with a binding moiety other than the targeted genome manipulating agent being tested. For example, in some aspects of the disclosure, cleavage efficiency parameters may be comparatively analyzed by functionalizing the first chip-based biosensor with a version of the targeted genomic manipulating agent where the blocking agent is omitted from the first aliquot, and both the first chip-based biosensor and the second based biosensor use the same targeting component (e.g., the same gRNA) where the genome manipulating component functionalized to the capture surfaces associated with the first chip-based biosensor is configured not to cleave the nucleic acid sample and the genome manipulating component functionalized capture surfaces associated with the second chip-based biosensor is configured to cleave the nucleic acid sample. With this arrangement, cleavage efficiency parameters can be comparatively analyzed. For example, cleavage parameters could be compared using identical nucleic acid sample aliquots and identical RNAs by selecting a deactivated manipulating component such as CRISPR-dCas9 for incubating the nucleic acid sample on the first chip-based biosensor and selecting a manipulating component that is purported to perform cleaving such as CRISPR-Cas9.

In some implementations, the first aliquot 108a and the second aliquot 108b are manually prepared in sample vessels such as for example PCR tubes or other selected containers. In other implementations, the first aliquot 108a and the second aliquot 108b are automatically or semi-automatically prepared by a sample prep apparatus 112 that includes automated dispensing such as performed by a dispensing robot and/or a fluidic system. In such implementations, the sample prep apparatus 112 may include its own controller and user interface for setting the time, temperature, and so forth of the incubation. In other implementations, the sample prep apparatus 112 may receive commands over the data network 122 from another device such as the computing device 114 or even the biomolecular measurement apparatus 102.

Certain implementations of the biomolecular measurement apparatus 102 may vary depending upon the technology used to sense biomolecular interactions between the nucleic acid sample and the targeted genome manipulating agent. For example, in implementations where the chip-based biosensors 104a, 104b use field-effect biosensing, as depicted for example in the apparatus 400 of FIG. 4), the biomolecular binding and/or cleavage interactions of a label-free nucleic acid sample can be measured without the need for a flow cell or fluid propulsion mechanisms to perform measurements. In other implementations, the biomolecular measurement apparatus 102 uses a chip-based biosensor 104 that includes a flow cell. Thus, various implementations of the apparatuses, systems, and methods described herein may be used in accordance with one or more implementations of the disclosure. The biomolecular measurement apparatus 102 is described in more detail below in the description of the apparatus 200 depicted in FIG. 2 and the apparatus 400 depicted in FIG. 4. In certain implementations, the biosensors 104 may include (but not by way of limitation) various types of chip-based biosensors that use terahertz spectroscopy, surface-enhanced spectroscopy, quartz crystal microbalance, grating-coupled interferometry, and so forth.

The system 100, includes an analysis module 116. In some implementations, the analysis module 116 is implemented using the computing device 114. In various implementations, the analysis module 116 is configured to determine one or more genome manipulating efficiency parameters associated with the targeted genome manipulating agent based on performing a comparative analysis of first and second response signals which may be first and second sets of response signals produced by the measurement controller 124 of the biomolecular measurement apparatus 102.

In certain implementations, the analysis module 116 may be programmed to perform comparative analyses between genome manipulating efficiency parameters determined using the chip-based biosensors and corresponding genome manipulating efficiency parameters determined using one or more other methods such as the various in silico, in vitro, and in vivo methods described above. For example, after performing fragmenting and adapter ligation in accordance with one or more of the methods 800, 900, 1000, 1100, and 1200 described below, the analysis results of the chip-based biosensors may be comparatively analyzed with one or more of the in vivo, in vitro, and/or in silico binding and/or cleavage efficiency results obtained for the same or similar targeted genome manipulating agent using any of the techniques described above. Thus, various systems, apparatuses, and methods of the present disclosure improve such in vivo, in vitro, and/or in silico binding and/or cleavage efficiency determination technologies by enhancing the selection of efficient targeted genome manipulating agents and further improve such technologies by providing independently derived data for comparative analysis with or validation using such technologies.

In certain implementations, the analysis module may be implemented on a device that is separate from the biomolecular measurement apparatus 102. For example, in certain implementations, the analysis module 116 is implemented on the computing device 114. The computing device 114 may be a laptop computer, desktop computer, a smartphone, a handheld computing device, a tablet computing device, a virtual computer, or an embedded computing device integrated into an instrument. The computing device includes a processor 218, memory 220, communication interface 222, and a keyboard display or similar visual output. In some implementations, the analysis module 116 is implemented completely within the computing device and other implementations the analysis module 116 is implemented at least in part in the biomolecular measurement apparatus 102.

In implementations where the analysis module 116 is implemented on the computing device 114, the computing device 114 may communicate with the measurement controller 124 over the data network 122. Similarly, the analysis module 116 may communicate data to other components of the system such as for example the enrichment apparatus 118, the sequencing apparatus 120, and/or the sample prep apparatus 112.

In some implementations, the computing device 114 is part of the biomolecular measurement apparatus 102 and may utilize the processor, memory, and communication interfaces of the biomolecular measurement apparatus 102 to measure the first and second response signals or first and second sets of response signals produced respectively by the first and second chip-based biosensors 104a and 104b in response to the biomolecular binding interactions occurring between the nucleic acid sample in the first and second aliquots and the targeted genome manipulating agent on the functionalized capture surfaces of first and second chip-based biosensors. In certain implementations, the analysis module 116 may be implemented as an embedded processor system or other integrated circuits that form part of the chip-based biosensor 104a, 104b.

In one example implementation, the analysis module 116 may be configured to perform a comparative analysis of the first and second response signal sets from identically prepared biosensors exposed to different solutions, such as when the first chip-based biosensor 104a is exposed to first aliquot 108a of the nucleic acid sample 108 that has been incubated with the blocking agent 110, and the second chip-based biosensor 104b is exposed to the second aliquot 108b of the same nucleic acid sample 108 that omits the blocking agent 110. In this case, the analysis module 116 may be configured to determine probability distributions for the concentrations of the detected nucleic acids according to an empirical model determined by calibration measurements of identically prepared biosensors exposed to target nucleic acids at known concentrations.

The analysis module 116 may then, in certain implementations, determine a probability distribution of the concentration of off-target DNA by subtracting the calculated concentration probability distribution of DNA from the first aliquot 108a with the blocking agent 110 (measured using the first chip-based biosensor 104a) from the concentration probability distribution of DNA (or other nucleic acid) from the second aliquot 108b without the blocking agent 110 (measured using the second chip-based biosensor 104b).

In some implementations, the analysis module 116 may be configured to comparatively analyze the time dependence of the first and second response signal sets, such as when the first chip-based biosensor 104a is prepared (e.g., functionalized) with dcas9, and the second chip-based biosensor 104b is prepared with cas9 with the same gRNA as the first chip chip-based biosensor 104b, and exposing both the first and second chip-based biosensors 104a, 104b to identical analytes (e.g., nucleic acid sample 108) to determine the cleaving rate of cas9 exposed to the nucleic acid sample 108 at known concentrations. The observed changes in the first and second response signals or first and second sets of response signals, such as drain current, capacitance, and so forth can be analyzed statistically, such as for example, by computing histograms of the first and second signal to determine the amount of time the nucleic acid sample (e.g., DNA) is bound to the chip-based biosensors 104a,104b.

The analysis module 116 may be configured to convert the first and second sets of response signal values into frequency space through the use of algorithms such as fast Fourier transforms, to determine the frequency of cleavage. These examples are non-limiting, and both types of analyses have general use in biosensors prepared identically or non-identically, and in measurements of first and second aliquots 108a, 108b prepared identically or non-identically.

In various implementations, the system 100 may include only some of the items depicted in FIG. 1, such as for example, the biomolecular measurement apparatus 102, the measurement controller 124, and the analysis module 116 which may be implemented on the computing device 114 in some implementations or the biomolecular measurement apparatus 102.

Figure 2:
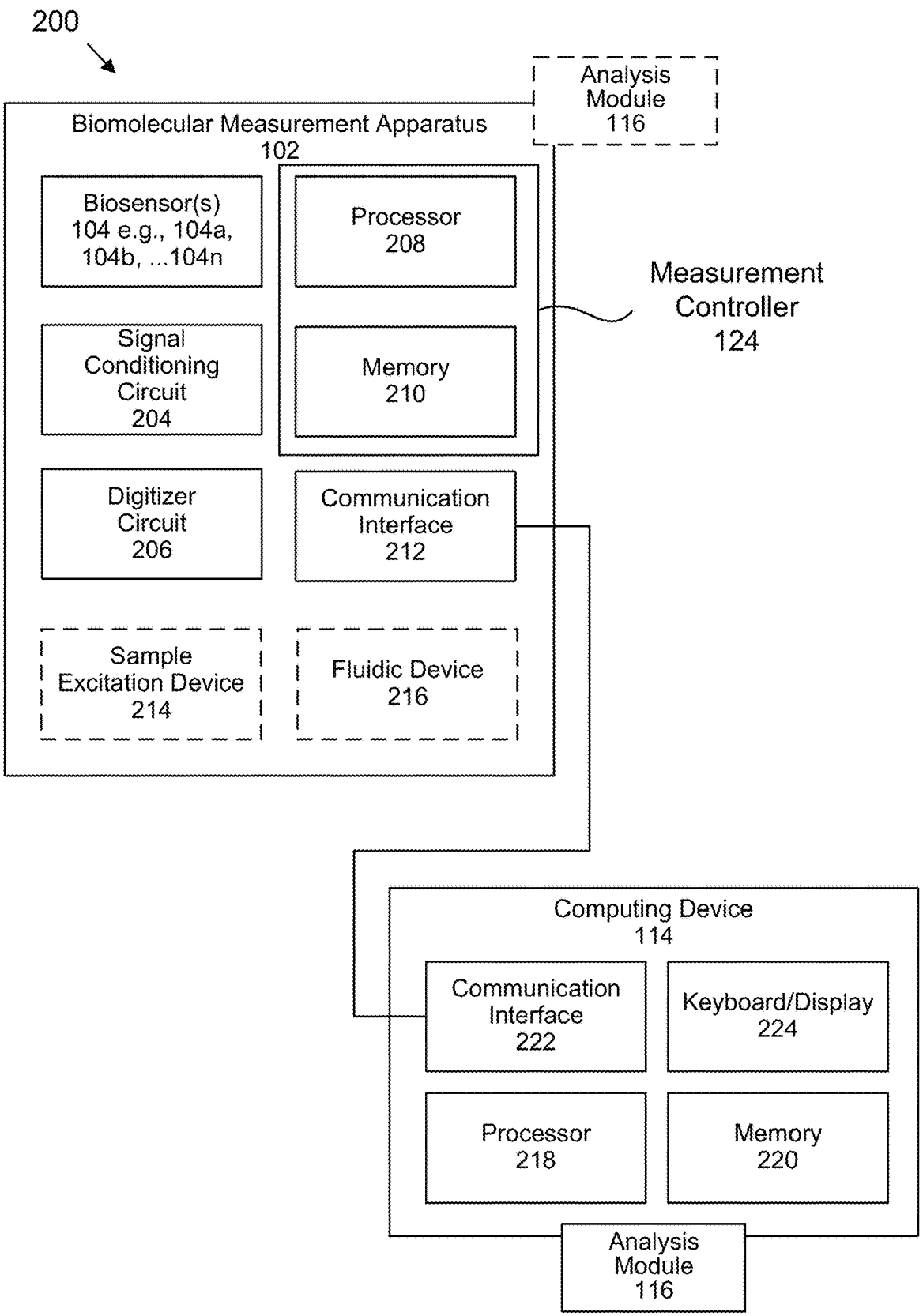
FIG. 2 is a schematic block diagram illustrating an apparatus for enhanced selection of an efficient targeted genome manipulating agent, according to one or more aspects of the present disclosure.

FIG. 2 is a schematic block diagram illustrating an apparatus 200 for enhanced selection of an efficient targeted genome manipulating agent, according to one or more aspects of the present disclosure. In one implementation, the apparatus 200 includes an instance of the biomolecular measurement apparatus 102. In various implementations, the biomolecular measurement apparatus 102 includes biosensors 104 such as the first chip-based biosensor 104a and the second chip-based biosensor 104b. The biomolecular measurement apparatus 102 also includes, in various implementations, one or more of the following: a signal conditioning circuit 204, a digitizer circuit 206, a processor 208, a memory 210 and a communication interface 212. In certain implementations, the biomolecular measurement apparatus 102 also includes one or more sample excitation devices 214 and one or more fluidic devices 216.

In some implementations, the fluidic devices 216 may be used to drive sample flow through a flow cell or other fluidic or microfluidic channels. The biology gated transistor implementation depicted in FIG. 4 may also use a flow cell if desired but because of the high-sensitivity of the biology gated transistor, no flow cell is needed to perform high-sensitivity measurements.

Figure 4:
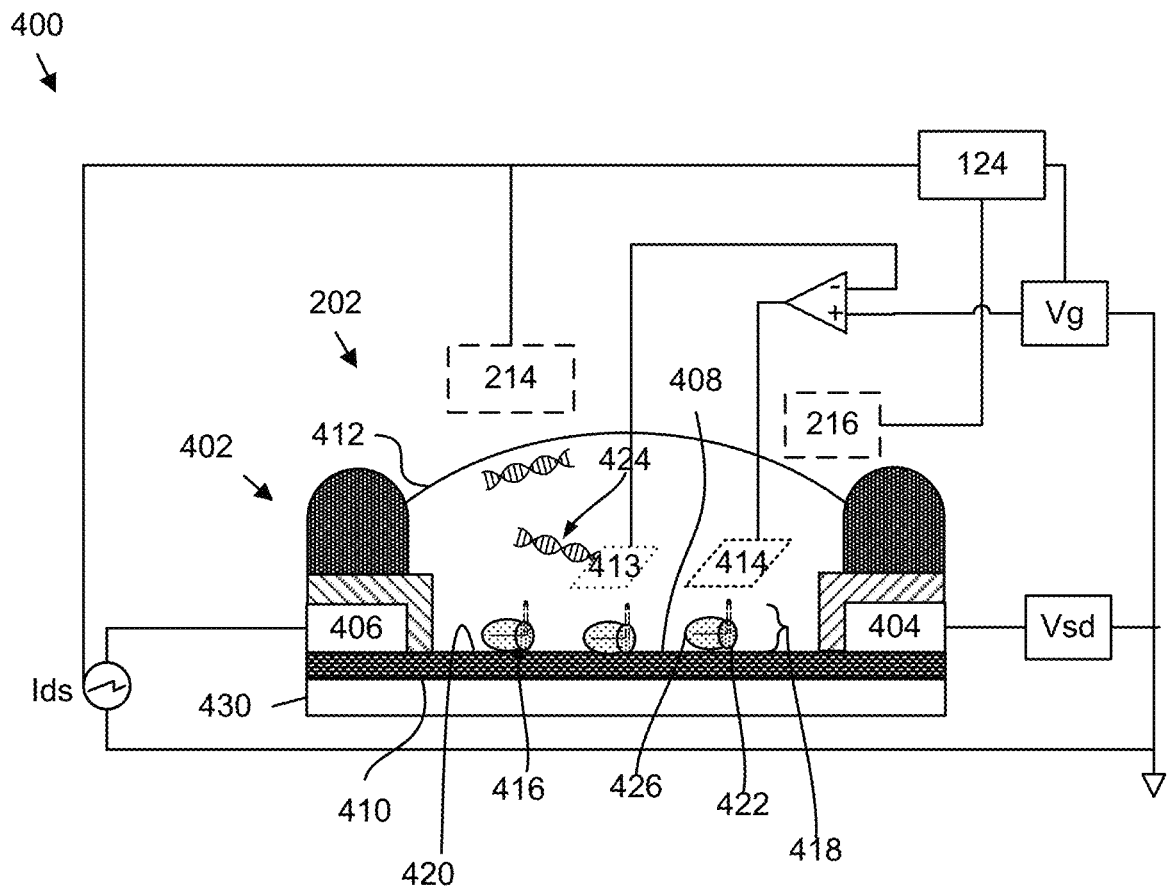
FIG. 4 is a diagram illustrating an example implementation of using a chip-based biosensor having a biology gated transistor for enhanced selection of an efficient targeted genome manipulating agent, according to one or more aspects of the present disclosure.

The biosensors 104, in various implementations, include the first chip-based biosensor 104a and the second chip-based biosensor 104b that are configured to perform label-free sensing of biomolecular interactions between the nucleic acid sample 108 and the functionalized capture surfaces 126 of the biosensors 104. Various types and technologies of chip-based biosensors 104a, 104b may be used in accordance with one or more aspects of the disclosure. For example, the apparatus 400 depicted in FIG. 4 depicts one implementation of a chip-based biosensor that uses field-effect biosensing technology for label-free detection of biomolecular binding interactions.

In such implementations, various biosensor parameters, such as for example, drain current, electrochemical current e.g. gate current, gate capacitance, drain impedance, gate impedance, transconductance, gate curve nonlinearity, gate curve hysteresis, Hall effect voltage, magnetoresistance, and so forth may be measured to produce first and second response signals which may be first and second sets of response signals.

In some implementations, the one or more sample excitation devices 214 are configured to subject the nucleic acid samples more types of excitation such as for example, magnetic excitation, electromagnetic excitation e.g., light, radio waves, ionizing electromagnetic or other radiation such as ultraviolet light, x-rays, gamma rays, electron beams, and so forth, physical excitation, e.g. ultrasound or agitation, electrical excitation such as for example a modulated gate bias voltage, temperature excitation such as for example a Peltier device for controlling heating and cooling of the chip-based biosensor, and so forth within a predetermined range of the electromagnetic spectrum. In certain implementations, these sample excitation devices 214 may be controlled by the measurement controller 124.

In certain implementations, the analysis module 116 may be implemented as described above using the processor 208, the memory 210 and/or the communication interface 212. In other implementations, the analysis module 116 may be implemented using the computing device 114. In certain implementations, the analysis module 116 may be configured to perform a comparative analysis of the first and second response signal sets from identically prepared biosensors exposed to different solutions, such as when the first chip-based biosensor 104a is exposed to first aliquot 108a of the nucleic acid sample 108 that has been incubated with the blocking agent 110, and the second chip-based biosensor 104b is exposed to the second aliquot 108b of the same nucleic acid sample 108 that omits the blocking agent 110. In this case, the analysis module 116 may be configured to determine probability distributions for the concentrations of the detected nucleic acids according to an empirical model determined by calibration measurements of identically prepared biosensors exposed to target nucleic acids at known concentrations.

The analysis module 116 may then, in certain implementations, determine a probability distribution of the concentration of off-target bound nucleic acid (e.g., DNA) by subtracting the calculated concentration probability distribution of the DNA from the first aliquot 108a with the blocking agent 110 (measured using the first chip-based biosensor 104a) from the concentration probability distribution of DNA (or other nucleic acid) from the second aliquot 108b without the blocking agent 110 (measured using the second chip-based biosensor 104b).

In some implementations, the analysis module 116 may be configured to comparatively analyze the time dependence of the first and second response signal sets, such as when the first chip-based biosensor 104a is prepared (e.g., functionalized) with dcas9, and the second chip-based biosensor 104b is prepared with cas9 with the same gRNA as the first chip chip-based biosensor 104b, and exposing both the first and second chip-based biosensors 104a, 104b to identical analytes (e.g., nucleic acid sample 108) to determine the cleaving rate of cas9 exposed to the nucleic acid sample 108 at known concentrations. The observed changes in the first and second response signals or first and second sets of response signals, such as drain current, capacitance, and so forth can be analyzed statistically, such as for example, by computing histograms of the first and second signal to determine the amount of time the nucleic acid sample (e.g., DNA) is bound to the chip-based biosensors 104a,104b.

The analysis module 116 may be configured to convert the first and second sets of response signal values into frequency space through the use of algorithms such as fast Fourier transforms, to determine the frequency of cleavage. These examples are non-limiting, and both types of analyses have general use in biosensors prepared identically or non-identically, and in measurements of first and second aliquots 108a, 108b prepared identically or non-identically. Although the systems, methods, apparatuses described herein may be utilized a variety of chip-based biosensors, implementations using field-effect biosensing technology, such as illustrated in FIG. 4, provide significant advantages in instrumentation cost, biosensor cost, precision, sampling time, and so forth because no precision optics or fluidics are required for field-effect biosensing.

Figure 3A:
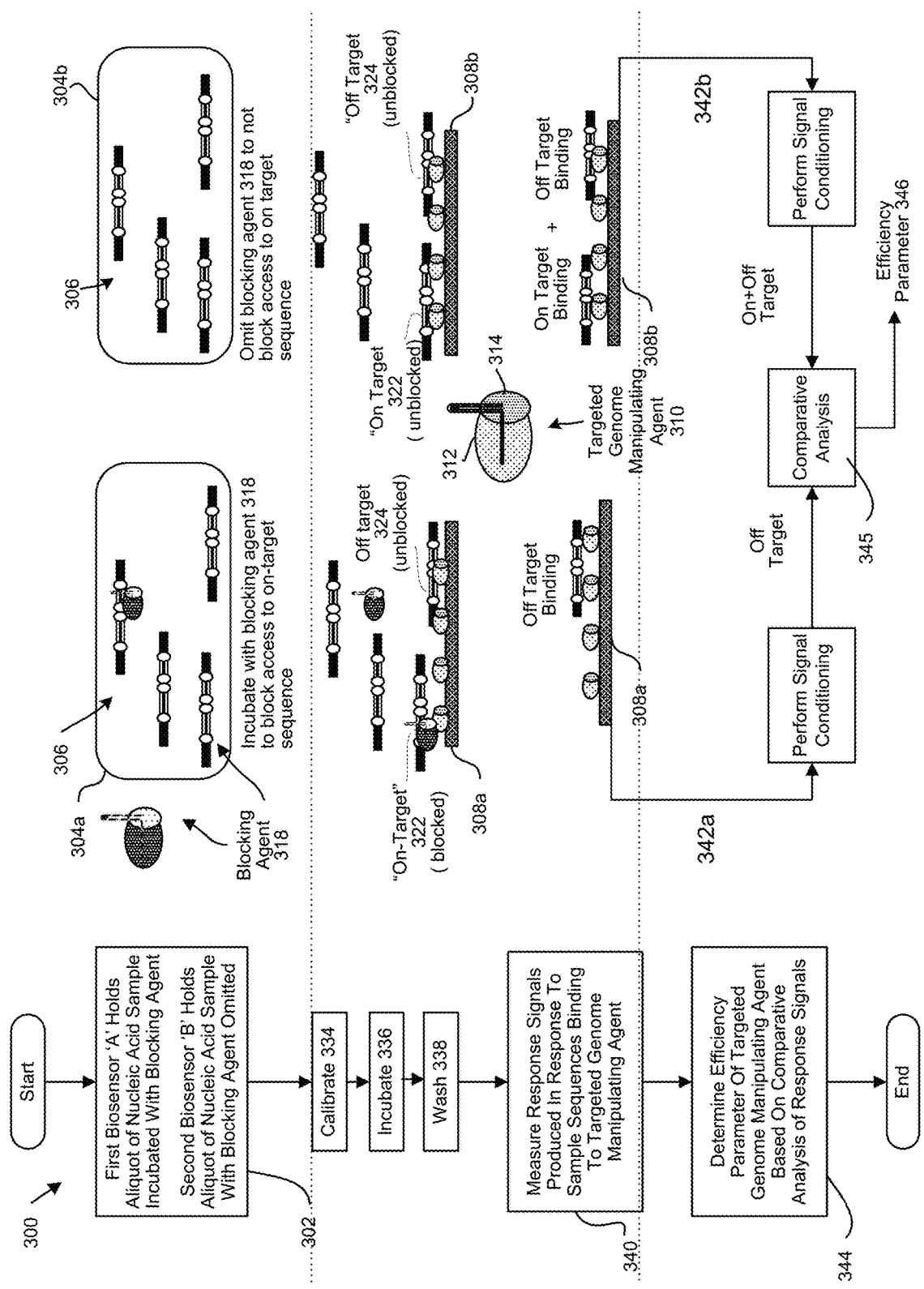
FIG. 3A is a diagram illustrating a method for enhanced selection of an efficient targeted genome manipulating agent, according to one or more aspects of the present disclosure.
Figure 3B:
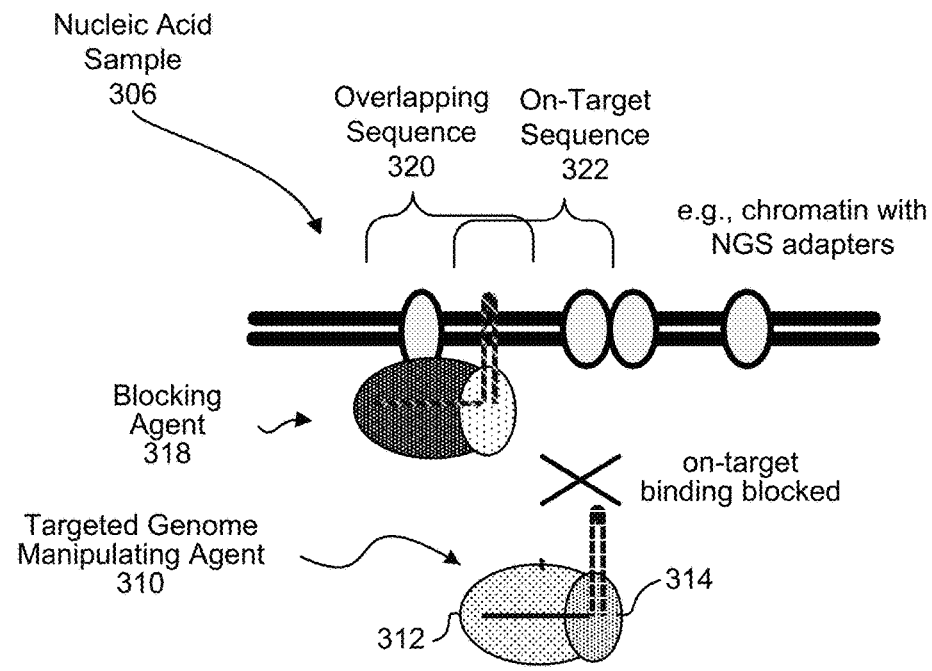
FIG. 3B is an enlarged detail diagram illustrating an example implementation of a blocking agent according to one or more aspects of the present disclosure.
Figure 3B:
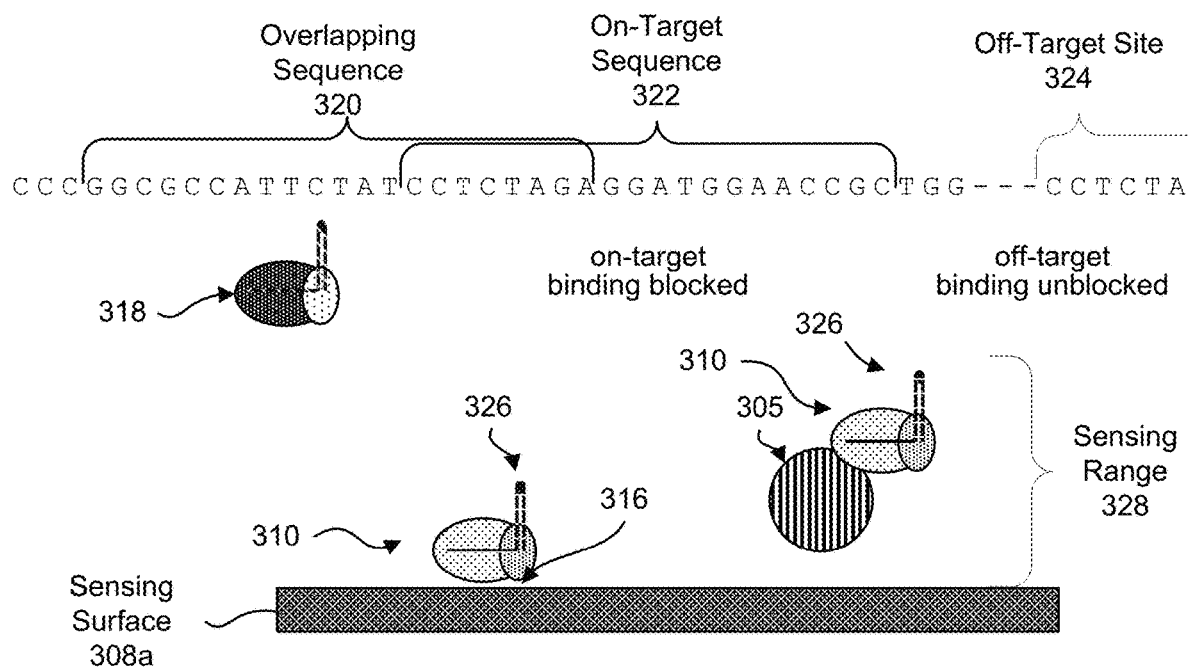

FIG. 3A is a diagram illustrating a method 300 for enhanced selection of an efficient targeted genome manipulating agent 310, according to one or more aspects of the present disclosure. FIG. 3B is an enlarged detail diagram illustrating an example implementation of a blocking agent according to one or more aspects of the present disclosure.

In one embodiment, the method 300 begins and includes preparing 302 a first aliquot 304a and a second aliquot 304b each comprising a nucleic acid sample 306 to be measured for detecting biomolecular binding interactions between the nucleic acid sample 306 dispensed to one or more sensing surfaces 308a, 308b and a targeted genome manipulating agent 310 that has a genome manipulating component 312 and a targeting component 314 and is functionalized to one or more capture surfaces 316 within a sensing range of the one or more sensing surfaces 308a, 308b.

In various implementations, the first aliquot 304a is optionally incubated with a blocking agent 318 configured to bind to an overlapping sequence 320 that overlaps an on-target sequence 322 of the nucleic acid sample 306 and the second aliquot 304b omits the blocking agent 318. As illustrated in extended detail in FIG. 3B, incubating the first aliquot 304a with the blocking agent 318 effectively blocks binding between the on-target sequence 322 of nucleic acid sample 306. For example, in certain implementations, the blocking agent 318 effectively blocks on-target binding through steric hindrance caused by material near the on-target sequence, or by causing the DNA to take a shape incompatible with binding, or by directly covering at least a portion of the on-target sequence so that on-target binding between the nucleic acid sample with the blocking agent and the targeted genome manipulating agent 310 is minimized. Because of these blocking mechanisms, the measurable binding that occurs between the targeted genome manipulating agent 310 and the nucleic acid sample 306 will be binding at an off-target site 324.

In certain implementations, the targeting component 314 of the targeted genome manipulating agent 310 includes a guide RNA with a guide sequence 326 configured to bind complementarily to the on-target sequence 322 and the genome manipulating component 312 includes a CRISPR associated protein molecule, such as for example Cas9, Cas12, Cas13, or similar CRISPR Cas complex. In the implementations illustrated in FIG. 3A and FIG. 3B, the genome manipulating component 312 is depicted as a CRISPR-Cas9. However, in some implementations, a non-cleaving genome manipulating component 312 such as a dCas molecule may be used.

In various implementations, the sensing surfaces 308a, 308b includes the functionalized one or more capture surfaces 316. In certain implementations, the one or more capture surfaces 316 are the surfaces of beads 305 functionalized with the targeted genome manipulating agent 310 within a sensing range 328 of the one or more sensing surfaces 308a, 308b such as depicted in FIG. 3B. More details about the functionalization of the capture surfaces provided below with respect to the description of FIGS. 5A, 5B, and 5C.

In various implementations, the method 300 continues and includes measuring 340 one or more first and second response signals 342a, 342b produced in response to the biomolecular binding interactions occurring between the nucleic acid sample 306 in the first and second aliquots 304a, 304b, and the targeted genome manipulating agent 310 on the functionalized one or more capture surfaces 316 of first and second chip-based biosensors 104a, 104b. In some implementations, the method 300 includes calibrating 334 the chip-based biosensors 104a, 104b prior to incubating 336 the first aliquot 108a (blocked) and the second aliquot 108b (unblocked). Calibrating 334 the chip-based biosensors 104a, 104b, provides a normalized baseline for the first and second response signals 342a, 342b.

In various implementations, the method 300 also includes washing 338 unbound portions of the nucleic acid sample 306. In the case of the first aliquot 304a (blocked) the DNA with the on-target segments 332 are washed 338 away and the portions of the nucleic acid sample 306 which exhibit off-target binding remain. Thus, the one or more first response signals 342a indicate binding parameters associated with off-target binding between the nucleic acid sample 306 incubated with the blocking agent 318 and the targeted genome manipulating agent 310 functionalized to the one or more capture surfaces 316 within the sensing range of the one or more sensing surfaces 308a.

For example, in implementations using biology gated transistors as the first and second biosensors a first response signal 342a such as the drain current or other parameters discussed in [0078] of a biology gated transistor of the first chip-based biosensor may be a monotonic function of the concentration of off-target binding present and a corresponding second response signal 342b of a biology gated transistor of the second chip-based biosensor may be a monotonic function of the concentration of on-plus-off target binding present. In certain implementations, various relations between the biology gated transistor parameters and the target concentration (e.g., the concentration of bound molecules whether on-target or off-target or both) may be calibrated beforehand using a representative sample of identically prepared biosensor chips. In some desirable implementations, the biology gated transistor response may be proportional to the concentration of DNA.

In certain implementations, such as implementations using field-effect biosensing as illustrated below with respect to the apparatus 400 depicted in FIG. 4, the one or more first and second response signals 342a, 342b are optionally measured using a sampling rate that satisfies a predetermined Nyquist criterion for measuring at least one parameter of the biomolecular binding interactions between the nucleic acid sample and the targeted genome manipulating agent over predetermined time period associated with the biomolecular binding interactions. In some implementations where the first and second response signals 342a, 342b involve measurements made using a biology gated transistor, the sampling rate may be programmable (e.g., using the measurement controller 124 of the apparatus 200 described above with respect to FIG. 2). In certain implementations, the predetermined Nyquist criterion may be based at least in part upon frequency-related characteristics (e.g., bandwidth) of the biomolecular binding interactions or components involved in the biomolecular binding interactions.

In some implementations, the predetermined Nyquist criterion may be based at least in part on frequency-related characteristics (e.g., bandwidth) of the measurement circuitry. For example, various implementations, the sampling rate is higher than the measurement bandwidth of the measurement circuitry so as to minimize artifacts such as aliasing. In certain implementations, where the sampling rate that satisfies the predetermined Nyquist criterion is high enough, the step of washing 338 may be omitted based on the additional precision and information gained by measuring 340 at the sampling rate that meets the predetermined Nyquist criterion.

In some embodiments, the method 300 continues and includes determining 344 an efficiency parameter 346 of the targeted genome manipulating agent based on comparing 345 the one or more first response signals 342a with the one or more second response signals 342b. For example, the response signals may be used to determine the concentrations of off-target DNA and on-plus-off target DNA, in which case a more accurate measurement of the on-target binding can be derived by subtracting the off-target binding values from the on-plus-off binding values.

FIG. 4 is a schematic block diagram illustrating an apparatus 400 that includes one implementation of a biosensor 202 in accordance with one or more examples of the present disclosure. In one implementation, the biosensor 202 is a chip-based biosensor that uses a biology gated transistor 402, also referred to as a liquid gate field effect transistor. In certain implementations, the biology gated transistor 402 includes a source electrode 404, a drain electrode 406, and a sensing surface 408 on a portion of a channel 410 that extends between the source electrode 404 and the drain electrode 406.

Instead of a gate electrode like those found in a conventional field-effect transistor, the biology gated transistor 402 has a liquid gate 412 that allows a drain source current Ids to flow through the channel 410 between the drain electrode 406 and the source electrode 404 based at least in part on an amount of charge in the liquid within a sensing range 418 of the sensing surface 408. In various implementations, a capture surface 420 is functionalized with a binding moiety. In certain implementations, for purposes of enhancing the selection of efficient targeted genome manipulating agents, the capture surface 420 is functionalized with a targeted genome manipulating agent 416 of interest. In other implementations, the capture surface 420 is functionalized with a nucleic acid sample 424 having a target of interest. In further implementations, the capture surface 420 comprises functionalized beads that capture a target of interest of the nucleic acid sample 424 within the sensing range 418 of the sensing surface 408.

In response to biomolecular binding interactions occurring between the nucleic acid sample 424 and the targeted genome manipulating agent 416, the sensing surface 408 is configured to detect even slight changes in charge or other transistor parameters brought about by the biomolecular binding interactions within the sensing range 418. Those detected changes in charge or other transistor parameters produce measurable response signals, such as for example, changes in drain current, gate current, drain impedance, gate impedance, transconductance, gate hysteresis, gate curve nonlinearity, gate curve hysteresis, Hall effect voltage, and magnetoresistance.

In some implementations, the apparatus 400 includes a reference electrode 413 for detecting the potential of the liquid gate 412. In certain example implementations, the biosensor 202 includes a counter electrode 414 for adjusting the potential of the liquid gate 412. In certain implementations, the measurement controller 124 is configured to modulate the counter electrode 414 at a rate that can be incrementally and programmatically adjusted to determine how the biomolecular interactions between the nucleic acid sample 424 and the targeted genome manipulation agent 416.

In various implementations, the channel 410 may be layered with a support layer 430, such as for example, a silicon dioxide layer. In certain implementations, the channel 410 is made of a highly sensitive conducting material such as graphene. In some implementations, the channel 410 uses other two-dimensional materials (sometimes also referred to as van der Waals materials e.g., materials having strong in-plane covalent bonding and weak interlayer interactions), such as for example, graphene nanoribbons (GNR), bilayer graphene, phosphorene, stanine, graphene oxide, reduced graphene, fluorographene, molybdenum disulfide, topological insulators, and so forth. Various materials that conduct and exhibit field-effect properties and are stable at room temperature when directly exposed to various solutions may be used in biology gated transistors (e.g., as a sensing surface or portion thereof). In various implementations, using biology gated transistors that utilize planar two-dimensional van der Waals materials improves manufacturability, and lowers costs compared with one-dimensional alternatives, such as carbon nanotubes.

In some implementations, the measurement controller 124 depicted in FIG. 1 is configured to measure the drain current Ids and/or other biology gated transistor parameters and to generate one or more response signals that can be further conditioned e.g. using the signal conditioning circuit 204. The digitizer circuit 206 depicted in FIG. 2 is configured to convert the one or more response signals into digital signals that can be stored, analyzed, and processed together with other response signals. In some implementations, various other parameters of the biology gated transistor are also measurable and/or convertible to response signals that can be measured, recorded, conditioned, digitized, and comparatively analyzed.

The targeted genome manipulating agent 416 includes a manipulating component 426 and the targeting component 422 configured to manipulate (e.g., cleave, block) the nucleic acid sample 424 at a site of a predetermined sequence complementary to the targeting component 422. The binding of the nucleic acid sample 424 may be at an "on-target" site of the genome if the on-target sites of the nucleic acid sample 424 are not blocks by a blocking agent or the binding of the nucleic acid sample 424 may be at an off-target site if the on-target site of the nucleic acid sample 424 is blocked by the blocking agent 428.

In certain implementations, the apparatus 400 includes the measurement controller 124 which is configured to control various devices, electrodes, signal conditioning, amplifiers, and so forth, of the biosensor 202. For example, in addition to controlling the gate voltage Vg for incremental adjustment and measuring, in some embodiments, the measurement controller 124 may apply and/or incrementally adjust a modulated liquid gate bias voltage for adjusting the sensing range of the biosensor, e.g., as affected by the Debye layer which is described in more detail below.

In other implementations, the measurement controller 124 may control one or more sample excitation devices 214, such as for example a resistive heater which may be useful for raising the temperature of the biological sample to predetermined temperature in order to determine how the biomolecular interactions occur at the predetermined body temperature. This may also be done on-chip using integrated devices, such as resistive wires used as Joule heaters and thermistors.

In certain implementations, the analysis module 116 may be programmed to perform comparative analyses between certain genome manipulating efficiency parameters determined using the chip-based biosensors described in the present disclosure and corresponding genome manipulating efficiency parameters determined using one or more other methods such as the various in silico, in vitro, and in vivo methods described above (e.g., Guide-Seq, Site-Seq and so forth). For example, after selecting one or more targeted genome manipulating agents using the comparative analysis of the first and second sets of response signals measured under conditions (e.g., body temperature, pH, and so forth) configured to align with corresponding conditions for another efficiency determining technology (e.g., one of the in vivo systems described above), and after performing fragmenting and adapter ligation in accordance with one or more of the methods 800, 900, 1000, 1100, and 1200 described below, the analysis module 116 may comparatively analyze the efficiency parameters determined using the results of the chip-based biosensors 104a, 104b with one or more of the in vivo, in vitro, and/or in silico binding and/or cleavage efficiency results obtained for the same or similar targeted genome manipulating agent using any of the techniques described above.

Thus, the various systems, apparatuses, and methods of the present disclosure improve such in vivo, in vitro, and/or in silico binding and/or cleavage efficiency determination technologies by enhancing the selection of efficient targeted genome manipulating agents and further improve such technologies by providing independently derived data for comparative analysis with or validation using such technologies.

As another nonlimiting example, the measurement controller 124 may control the sample excitation device 214 such as a Peltier device to cool the temperature of the sensing surface 408 and the nucleic acid sample in order to more precisely analyze the response of the biomolecular by the interactions to the cooling effects of the sample excitation device 214.

Other sample excitation devices 214 such as light emitters of any desired wavelength may be useful for measuring the effect of the excitation on the biomolecular binding interactions.

In certain implementations, where the capture surfaces are functionalized magnetic beads, the measurement controller 124 may control one or more electromagnets or mechanically positionable magnets to affect the position of the beads within the sensing range. The beads may be so positioned to come in contact with the biosensor surface for sensing purposes, and away from the surface for target-capturing purposes. These motions can result in the beads moving beyond the double layer so as to be undetectable by the sensor.

Figure 5A:
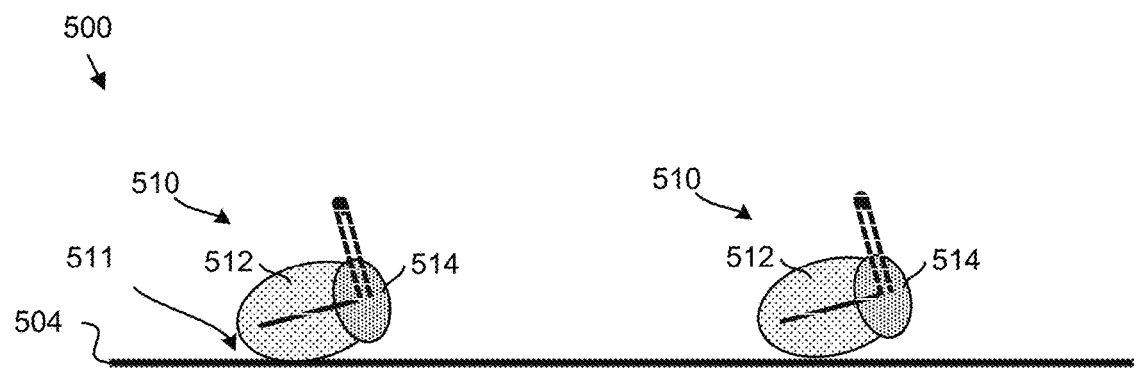
FIG. 5A illustrates an implementation of a capture surface functionalized with a targeted genome manipulating agent, according to one or more examples of the present disclosure.
Figure 5B:
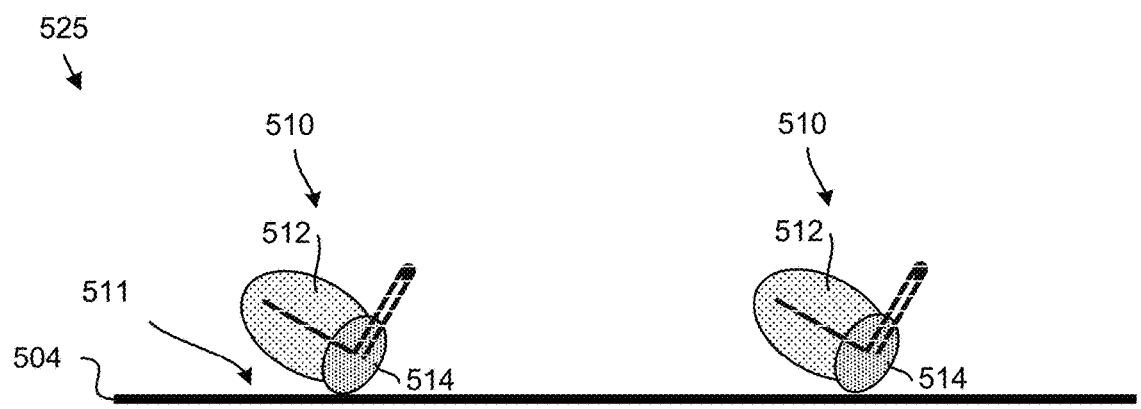
FIG. 5B illustrates an implementation of a capture surface functionalized with a targeted genome manipulating agent, according to one or more examples of the present disclosure.
Figure 5C:
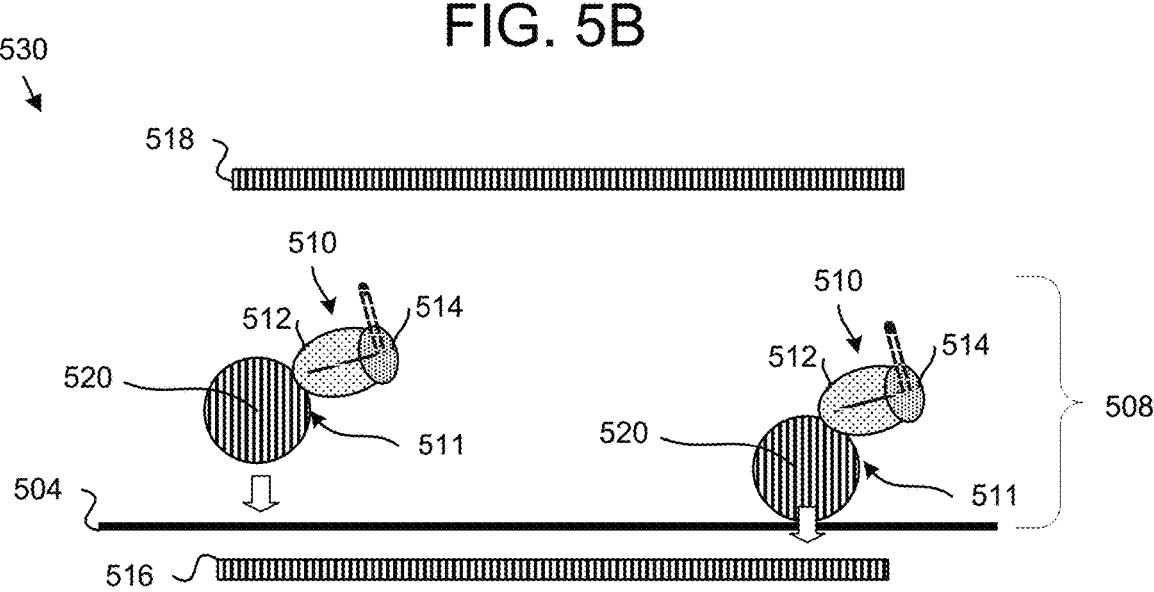
FIG. 5C illustrates an implementation of a sensing surface for detecting one or more capture surfaces functionalized with a targeted genome manipulating agent, according to one or more examples of the present disclosure.

FIGS. 5A, 5B, and 5C illustrate various implementations of capture surfaces 511 according to one or more examples of the present disclosure. In some implementations, the targeted genome manipulating agent 510 is functionalized to one or more capture surfaces 511. In certain implementations, the capture surface 511 is a part of the sensing surface 504. In one or more implementations, the capture surface 511 is a capture surface only and the assessing of binding and cleavage efficiency is done separately. In another embodiment, the capture surface 511 is a flat surface made of biocompatible materials that have low nucleic acid binding adsorption and low protein binding adsorption and are known to be used to be functionalized with proteins or DNA. Various examples of biocompatible materials include but are not limited to, glass, plastics, silicon, metals, or hydrogels, functionalized with the targeted genome manipulating agent 510. In a further embodiment, the capture surface 511 is a column made of the targeted genome manipulating agent 510 bound to a resin.

In some implementations, the targeted genome manipulation agent 510 includes a genome manipulating component 512 (e.g., a Cas protein such as dCas9 or Cas9) and a targeting component 514 (e.g., a guide RNA) where the targeting component 514 is configured to bind with an on-target site of a nucleic acid sample. In some implementations, the genome manipulating component 512 is active (e.g., Cas9) to perform cleaving of a nucleic acid at an on-target site of a nucleic acid sample. In certain implementations, the genome manipulating component 512 is inactive (e.g., dCas9) to perform on-target binding to a target site of a nucleic acid sample without cleavage.

FIG. 5A illustrates an implementation 500 of a capture surface 511 functionalized with a targeted genome manipulating agent 510, according to one or more examples of the present disclosure. In various implementations, the targeted genome manipulating agent 510 is functionalized to the capture surface 511 via the genome manipulating component 512 (e.g., a Cas protein). In certain implementations, the capture surface 511 is a portion of a sensing surface 504 of a biology gated transistor such as the biology gated transistor 402 depicted above with respect to FIG. 4. In other implementations, the sensing surface 504 is a surface of Surface Plasmon Resonance ("SPR") sensor chip, a terahertz spectroscopy sensor chip, a surface-enhanced spectroscopy sensor chip, quartz crystal microbalance sensor chip, a grating-coupled interferometry sensor chip, and so forth.

In some implementations, the sensing surface 504 includes graphene and the targeted genome manipulation agent 510 is functionalized to the capture surface 511 using an amine link between a graphene-decorated COOH surface of the sensing surface 504 and one or more amine (NH2) groups of the genome manipulating component 512 e.g. Cas9.

FIG. 5B illustrates an implementation 525 of a capture surface 511 functionalized with a targeted genome manipulating agent 510, according to one or more examples of the present disclosure. In one implementation, the targeted genome manipulating agent 510 is functionalized to the sensing surface 504 via the targeting component 514 (e.g., a gRNA portion of a Cas-gRNA complex). In the implementation 525 where the sensing surface 504 as part of a biology gated transistor such as depicted in FIG. 4, the targeted genome manipulating agent 503b (e.g., a Cas-gRNA complex) tethers to the sensing surface 504 (e.g. the graphene surface) via the targeting component 502b (e.g., the gRNA).

In a first gRNA tethering implementation, the targeting component 502b is a gRNA synthesized with an amino group at one end and is immobilized to a COOH chemistry decorating the sensing surface 504 (e.g., the graphene channel). In a second gRNA tethering implementation, the targeting component 502b is a gRNA synthesized with a biotin at one end and immobilized (e.g., tethered) to a streptavidin coating at the sensing surface 504. In a third gRNA tethering implementation, the targeting component 502b is a gRNA that is functionalized to the sensing surface 504 via Watson-Crick base pairing with an oligonucleotide bound to the sensing surface 504.

FIG. 5C, illustrates an implementation 530 of a sensing surface 504 for detecting biomolecular binding interactions between one or more capture surfaces 511 functionalized with a targeted genome manipulating agent 510, according to one or more examples of the present disclosure. In certain implementations, the one or more capture surfaces 511 are beads 520 having a size from about 1 nanometer (nanoparticle) to 1000 micrometers. In some implementations, the beads 520 are composed (at least on their outer surface) of materials that are biocompatible, providing low nucleic acid and protein binding adsorption, and known to be functionalized with proteins or DNA.

Such biocompatible materials include but are not limited to, glass, plastics, silicon, metals, or hydrogels, functionalized the targeted genome manipulating agent 510. In various implementations, the beads 520 can be nonmagnetic, magnetic or paramagnetic. In certain implementations, a first magnet 516 and a second magnet 518 may be disposed above and below the sensing surface. The first magnet 516 can be activated to attract the magnetic beads 520 toward the sensing surface 504 and the second magnet 518 can be activated to direct the magnetic beads 520 away from the sensing surface 504. Thus, by controlling the activation of the first magnet 516 and the second magnet 518, the functionalized targeted genome manipulation agents 510 may be moved up or down or otherwise agitated including in or out of the Debye layer In the implementation 530, the capture surface 511 is part of one or more functionalized beads 520 that allow binding to be sensed by the chip-based biosensor when biomolecular binding interactions occur between a nucleic acid sample and the targeted genome manipulating agent 510 that is functionalized to the capture surface 511 of the beads 520 is within a sensing range 508 of the sensing surface 504.

In various implementations, the sensing surface 504 is part of a chip-based biosensor configured to perform label-free detection of one or more components of a nucleic acid sample. FIG. 4 depicts an example implementation of a biosensor 202 that is chip-based and that performs field-effect biosensing using a biology gated transistor 402.

The one or more capture surfaces 511 may in certain implementations both sense and also capture target nucleic acid sequences of interest. In some implementations, nucleic acid samples captured by the capture surfaces 511 can be recovered providing enrichment of sequence targeted by the targeted genome manipulating agent 510.

Figure 6:
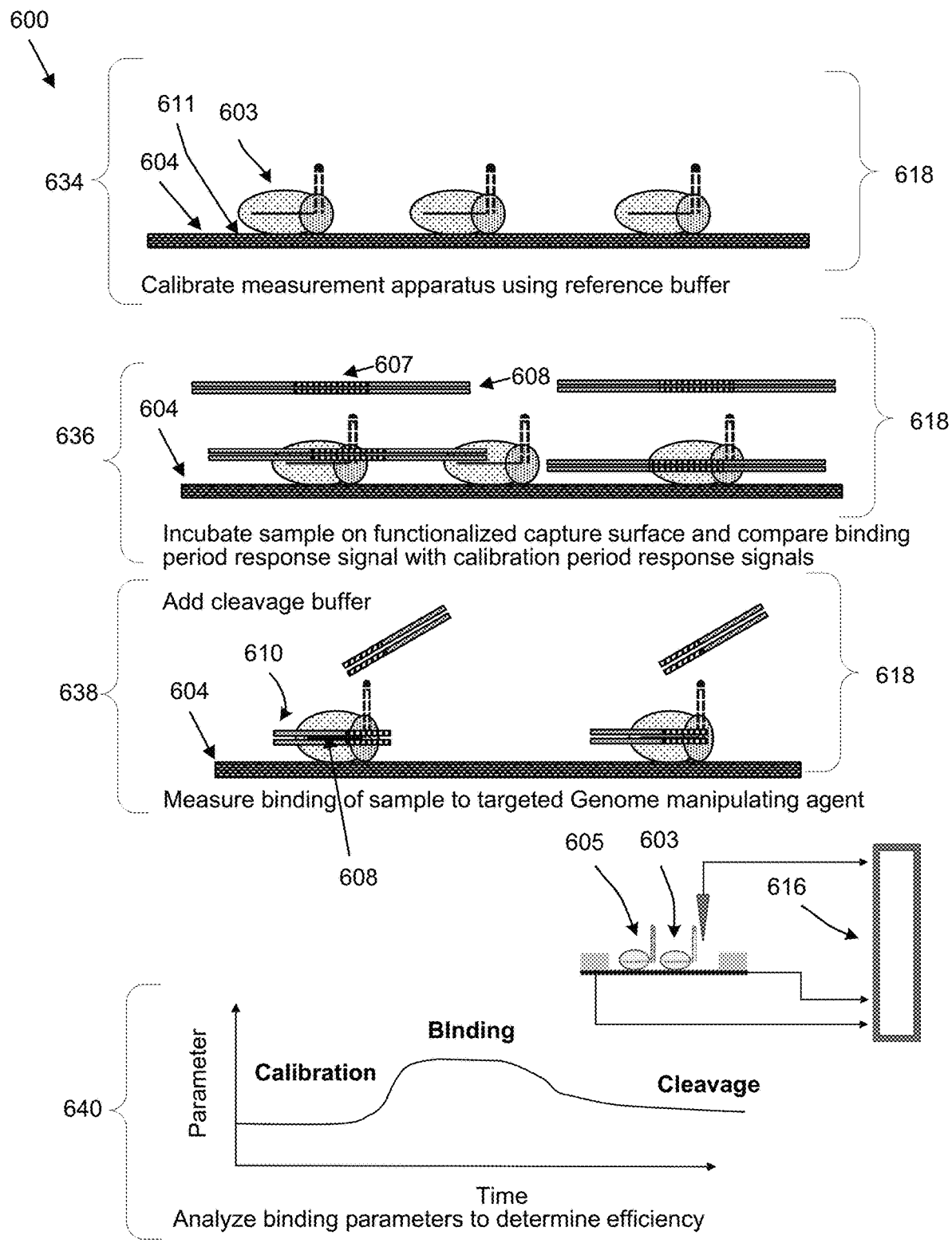
FIG. 6 illustrates a method for determining binding efficiency parameters for a targeted genome manipulating agent immobilized to a sensing surface, according to one or more examples of the present disclosure.

FIG. 6 illustrates a method 600 for determining binding efficiency parameters for a targeted genome manipulating agent immobilized to a sensing surface, according to one or more examples of the present disclosure. In one implementation, the method 600 begins and includes calibrating 632 the chip-based biosensor 605 with a reference buffer. Based on a response signal generated by the chip-based biosensor 605, the method displays a calibration baseline 540a which then serves as a reference against which changes in the charge of the liquid gate e.g., brought about by one or more biomolecular binding interactions within the sensing range 618 to be sensed by the chip-based biosensor 605. In various implementations, the method 600 includes enhancing the sensitivity of the chip-based biosensor 605 by using a low salt reference buffer to decrease the length or thickness of the Debye layer.

In one example, the method 600 for determining on-target binding parameters includes incubating 634 a nucleic acid sample 608 such as DNA using a chip-based biosensor 605 that has a functionalized capture surface 611 associated with the sensing surface 604 of the chip-based biosensor 605. In some examples, the targeted genome manipulating agent 603 is a Cas/gRNA complex that is functionalized onto the chip-based biosensor 104 that utilizes biology gated transistors, such as for example a graphene FET ("gFET").

In certain implementations, the chip-based biosensor 605 is a removable or non-removable chip that connects to an external or integrated electronic reader 616 configured to measure different transistor parameters that are affected by the binding of the targeted genome manipulating agent 603 e.g. the Cas9/gRNA complex and a target sequence 607 of the nucleic acid sample 608. In various implementations, the sensing surface 604 of the chip-based biosensor 605 detects negative and/or positive charges brought within the sensing range 618 by the capture of the nucleic acid sample 608 by the functionalize capture surface 611. In some implementations, the amount and polarity of charge can be controlled within biologically necessary bounds by changing the pH and ionic concentration of the buffer solution.

In some implementations, various parameters including parameters other than charge are affected by the presence of a captured nucleic acid molecule or fragment close to the sensing surface 604. Some such parameters include, for example, gate capacitance (e.g., $C_{gs}$, $C_{gd}$), drain current (e.g., "$I_{ds}$"), and gate voltage (e.g., "$V_{gs}$"). Using a response signal that indicates changes in capacitance, can, for example, enable detection of uncharged molecules.

In certain implementations, the reference buffer includes from about 1 mM to 20 mM NaCl and 0 mM to 20 mM EDTA. In some implementations, the reference buffer can be replaced by pure water. The method 600 continues and includes removing the reference buffer and incubating the nucleic acid sample 608 (e.g., DNA molecules) in a binding buffer favoring the recognition and binding of a target site of the nucleic acid sample 608 to the capture surface 611 functionalized with the targeted genome manipulation agent 603. In certain implementations, the binding buffer is selected to minimize cleavage of the captured nucleic acid at the target sequences 607. For example, in some implementations, the method includes adding a quencher molecule such as EDTA to the binding buffer in saturating quantity to quench di-cation such as $Mg2+$, $Mn2+$, $Fe2+$, $Co2+$, $Ni2+$ or $Zn2+$ if present in the solution. In one example, the binding buffer with the quencher molecule contains from about 1 mM to 500 mM NaCl, 0 mM to 100 mM HEPES, 100 mM to 1M EDTA, and the pH between 5 to 8.5.

In certain implementations, the method 600 continues and includes a binding step 636 for incubating the sample nucleic acid in the chip-based biosensor at room temperature for from about 1 minute to about 16 hours. The method 600 continues and after the incubation includes discarding the supernatant and washing the chip-based biosensor 605 from 1 to 10 times with a washing buffer. The washing buffer includes in various examples, from 1 mM to 500 mM NaCl and from 1 mM to 500 mM EDTA. In certain examples, the method 600 further includes incubating the sensing surface 604 of the field-effect biosensor again with the reference buffer and measuring new values for the selected parameters.

In one aspect, when a targeted genome manipulating agent 603 such as a Cas9/gRNA complex recognizes a predetermined target sequence 607 in an absence of magnesium, it binds tightly to the target sequence 607 without cutting it. Any charged molecules, such as in this example, the nucleic acid sample 608 e.g., DNA), which are tethered to the graphene surface induce a change of the parameters listed above. The method 600 continues and includes displaying, recording, and/or comparing differences of intensity of the parameters recorded before (e.g. during the calibration step 634 with reference buffer) and after the incubating of the nucleic acid sample 608 with the targeted genome manipulating agent. In various implementations, the method 600 includes determining an efficiency parameter of the targeted genome manipulating agent 603 based on comparing one or more first response signals measured in the calibration step 634 with one or more second response signals measured throughout the binding step 636.

Since DNA is a charged molecule, a DNA molecule laying inside the Debye layer may affect one or more of the parameters listed above. Accordingly, the method 600 determines 640 an efficiency parameter of the targeted genome manipulating agent 603 based on comparing the differences in the response signals from the incubation period to the calibration period proportional to the captured nucleic acid.

In various implementations, the method 600 continues and includes identifying the targeted genome manipulating agent 603 as having a suitable targeting component 602 in response to determining that a difference between the one or more response signals measured during the binding step 636 and the corresponding response signals measured during the calibration step 634 satisfies a predetermined binding efficiency condition. In other words, the greater the response measured during the binding step, the better the targeting component 602 (e.g. the gRNA) will be capturing its targeted DNA thus giving the user an indication to go further with this specific gRNA or in the case of the difference in the response signals failing to satisfy a predetermined binding efficiency condition indicating to the user a recommendation to design a new targeting component 602.

In various implementations, method 600 continues and includes applying 638 a cleavage buffer to the chip chip-based biosensor after recording the binding capabilities of targeted genome manipulation agent 603. In one example, the cleavage buffer includes 1 mM to 500 mM NaCl, 5 mM to 20 mM MgCl2, and 0 mM to 100 mM HEPES, with a pH between 5 to 8.5. In the presence of Mg2+ or other divalent cations such as Mn2+, Fe2+, Co2+, Ni2+ or Zn2+, the Cas9 cuts the DNA at the target sequence 607, e.g., its recognition site.

In response to a cleavage buffer being applied to the chip-based biosensor 605 after the binding step 636 measurements, a nucleic acid sample 608 such as DNA that is bound to the capture surface by an efficient targeted genome manipulation agent 603 is cut with high efficiency. The cutting induces a portion of the nucleic acid sample 609 to flow away from the sensing surface 604.

To determine a semi-quantitative or quantitative result, the method 600 includes incubating the targeted genome manipulation agent 603 (e.g., Cas9/gRNA immobilized complex) with the cleavage buffer at room temperature for from about 30 seconds to about 60 minutes and replacing the cleavage buffer with the reference buffer. Depending on the efficiency of the targeted genome manipulation agent being tested, the response signals of one or several parameters listed above will reach a cleavage level 638 between the first measurements made during the calibration step and a level of the response signals during the binding step 636. Since the genome manipulating component e.g., Cas9 is still bound to one end 610 of its substrate even after an efficient cleavage, the response signal should not reach the first reference measurement made during the calibration step 634.

In certain implementations, the method 600 continues and determines an overall efficiency of the targeted genome manipulating agent 603 based on comparing the differences relative to the calibration step of the measured response signal during the binding and cleavage. The greater the differences between the respective binding and cleavage response signals and the calibration response signals, the greater the indication to the user that the selected targeted genome manipulating agent 603 is efficient and can be further tested to determine whether it induces putative off-target binding over a genome of interest. In various examples, the nucleic acid sample 608 can be an amplicon, a strand of genomic DNA, chromatin or other types of nucleic acid such as RNA provided that an appropriate genome manipulating component 601 such as Cas13 is utilized with an appropriate targeting component 602.

Figure 7:
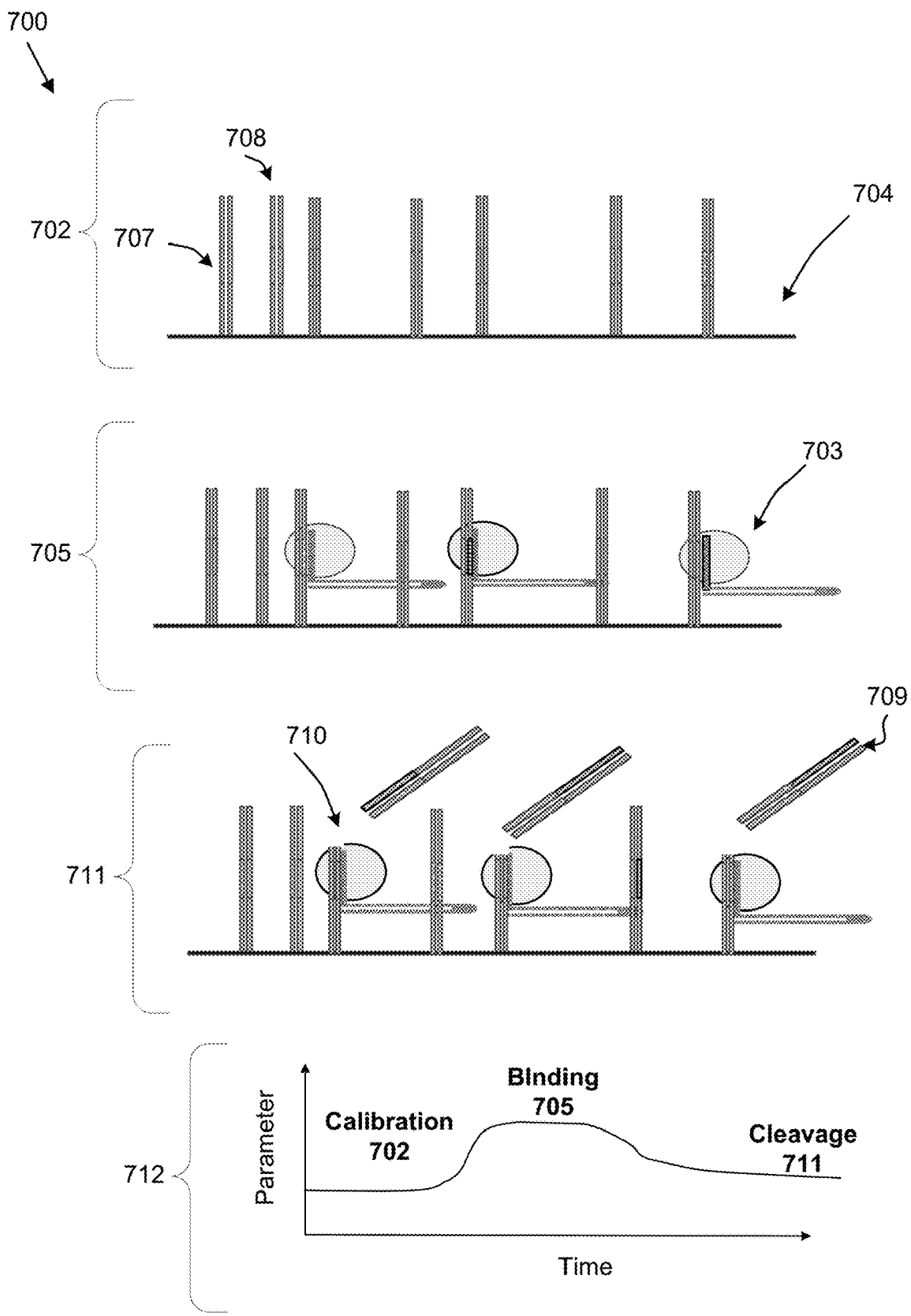
FIG. 7 illustrates a method for determining binding efficiency parameters for a targeted genome manipulating agent using a double-stranded nucleic acid immobilized to a sensing surface, according to one or more examples of the present disclosure.

FIG. 7 illustrates a method 700 for determining binding efficiency parameters for a targeted genome manipulating agent 703 using a double-stranded DNA 708 immobilized to a sensing surface 704, according to one or more examples of the present disclosure. In one implementation, the method 700 begins and includes providing 702 a chip-based biosensor that includes double-stranded DNA 708 immobilized to the sensing surface 704. The immobilized double-stranded DNA 708 contains an on-target sequence 707 to which the targeted genome manipulating agent 703 is configured to bind. The method 700 is performed using a similar calibration step 702, binding step 705, and cleavage step 711 where the targeted genome manipulating agent 703 cleaves a nucleic acid fragment 709 as described above with respect to the method 600 depicted in FIG. 6. However, in the method 600, the charges which the biology gated transistor sensor monitors are not the DNA charges but charges of the targeted genome manipulating agent 703 in response to binding with the dsDNA immobilized to the sensing surface 704. This method 700 is particularly useful when testing a genome manipulating component for cleavage efficiency such as for example engineered Cas9 or similar nuclease since the same functionalized sensing surface 704 can be used until a satisfactory targeted genome manipulating agent 703 e.g., Cas9/gRNA complex is identified. The method 700 continues and displays 712 response signals for the calibration step 702, the binding step 705, and the cleavage step 711. The response signals vary in relation to changes in the measured parameters (e.g., concentration of bound molecules) as described above.

Detection of putative off-target binding/cleavage activity. In response to determining, that a targeted genome manipulate agent satisfies one or more predetermined binding and cleavage efficiency parameters, for example where a Cas9/gRNA complex being tested shows good binding/cleavage activity, it is beneficial to check if the targeted genome manipulating agent targets off-target regions or sites of the genome for which it has been designed to be used. The system 100, apparatuses 200, 400, and the method 300 described above with respect to FIGS. 1 through 4 provide various ways to comparatively analyze on-target binding and off-target binding.

Figure 8:
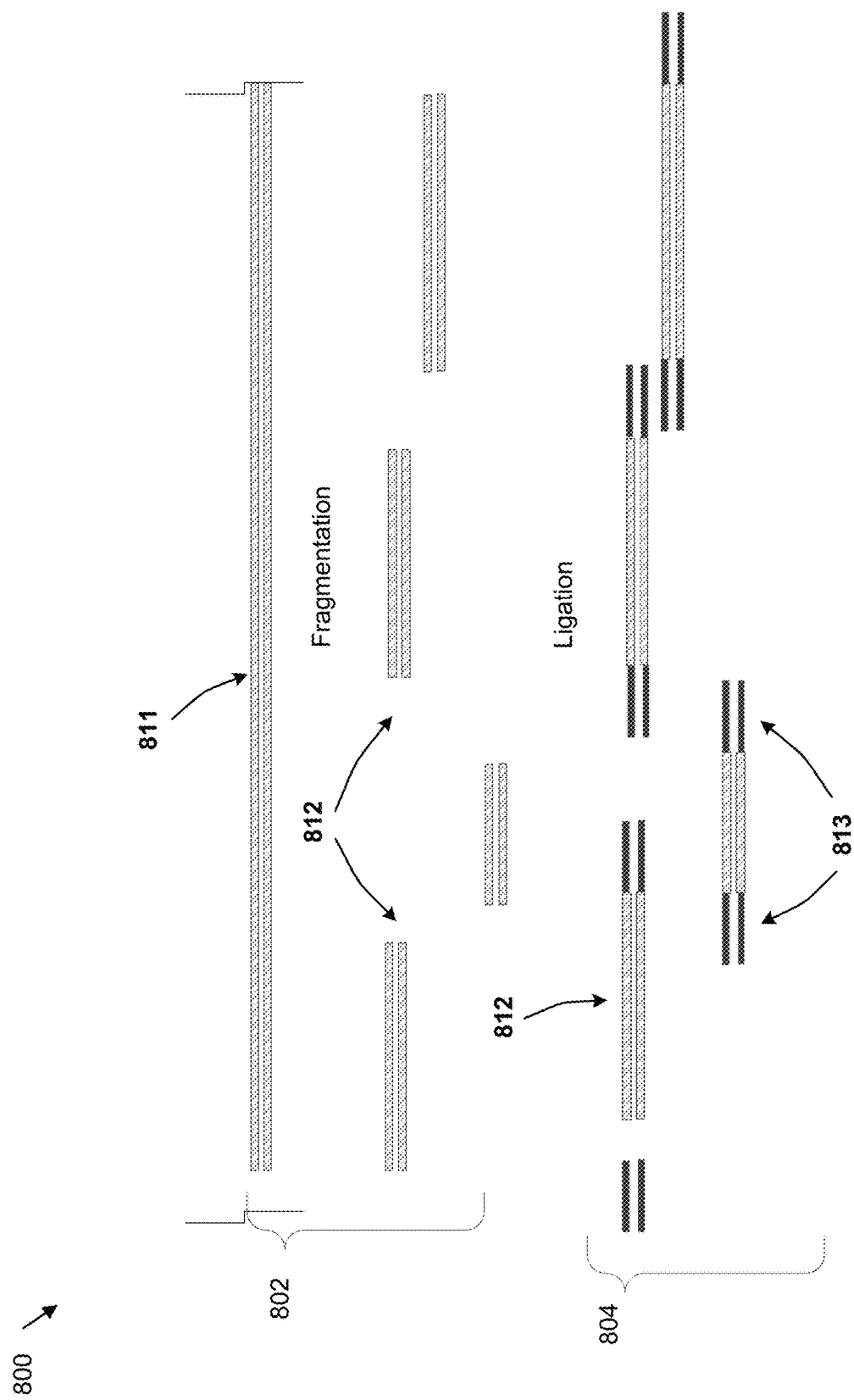
FIG. 8 illustrates fragmentation and adapter ligation of a nucleic acid sample for sequencing after measurement of a genome manipulating parameter, according to one or more examples of the present disclosure.

FIG. 8 illustrates one implementation of a method 800 for fragmenting DNA 812 and adapter ligation 813 of a nucleic acid sample 811 for sequencing after measurement of a genome manipulating efficiency parameter, according to one or more examples of the present disclosure. The method 800 begins and includes fragmenting 802 a nucleic acid sample 811 comprising full DNA that has been purified using known DNA purification technologies. The fragmenting 802 is performed using any suitable fragmenting technique such as for example sonication, acoustic shearing, hydrodynamic shearing, endonuclease digestion, and so forth. In various implementations, parameters of physical and enzymatical shearing are selected to produce DNA fragment comprise between 50 to 10 000 bp, more preferably between 100 and 1000 bp.

The method 800 continues and repairs 804 the fragmented DNA 812 using enzymes selected based on the mode of fragmentation used. For example, if the fragmented DNA 812 is fragmented using sonication, it is repaired using, for example, the T4 DNA polymerase in presence of dNTPs, that produce blunt ends by filling the 5' overhangs via its 5'→3' activity and filling the recess 3' overhangs via its 3'→5' exonuclease activity.

The method continues and includes ligating the fragmented DNA 812 to adapters 813 which are designed to be used with the NGS technology of the user choice. Each adapter 813 is designed to produce an overhanging end in one of its extremities and is modified with blocking moiety of both ends of the other extremity avoiding self-ligation and subsequent ligation when ligated in place with DNA fragment 812.

Figure 9:
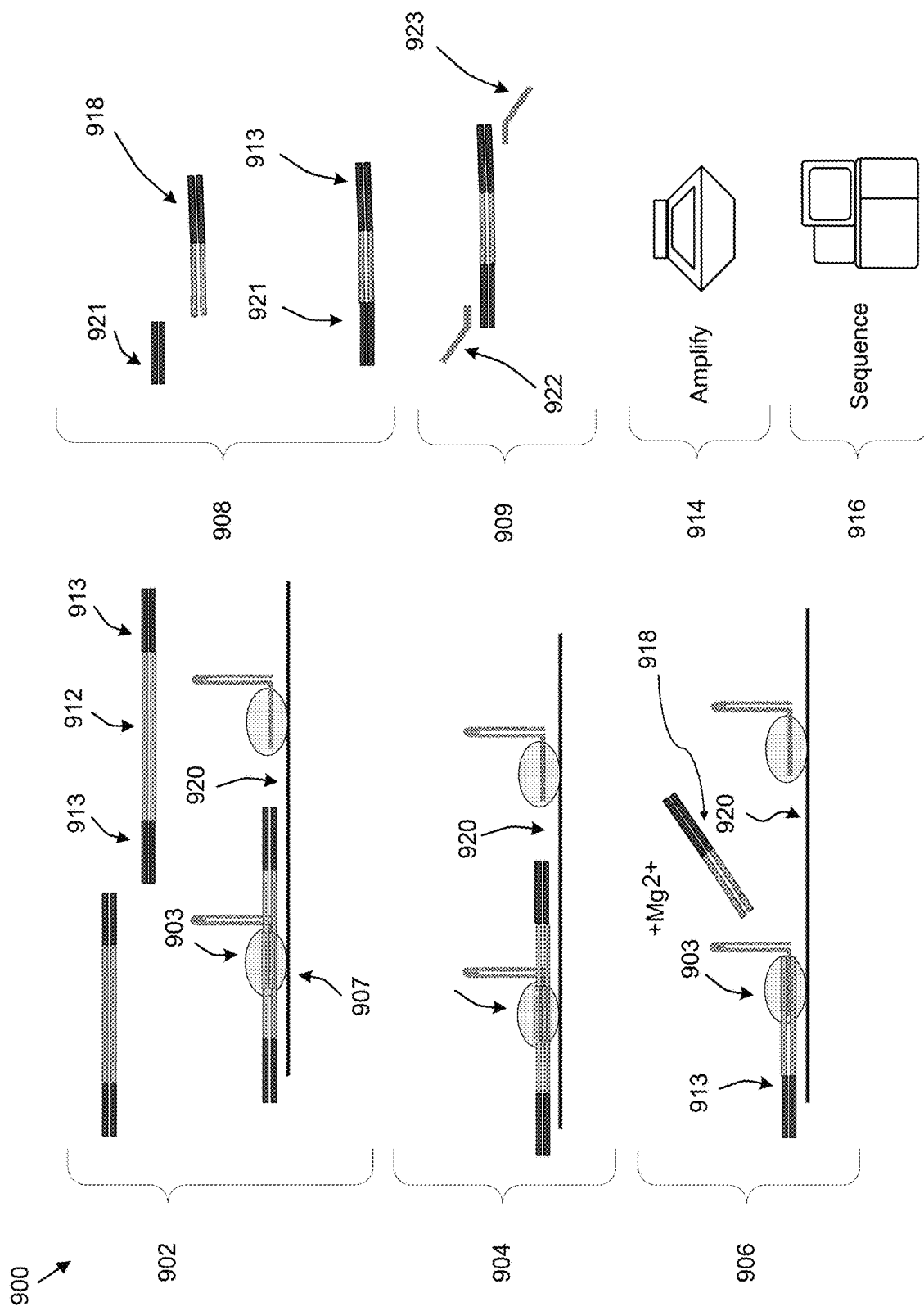
FIG. 9 illustrates fragmentation and adapter ligation of a nucleic acid sample for sequencing after measurement of a genome manipulating parameter, according to one or more examples of the present disclosure.

FIG. 9 illustrates another method 900 for preparing a fragmented and adapter-ligated nucleic acid sample for sequencing after measurement using the one or more chip-based biosensors of a genome manipulating parameter, according to one or more examples of the present disclosure.

The method 900 begins and includes incubating 902 a nucleic acid sample e.g., an adapter-linked native chromatin 912 that is fragmented and labeled with adapters 913. One or more instances of the adaptor-linked native chromatin 912 are incubated at a capture surface 920 that in some embodiments is a sensing surface of a chip-based biosensor. The capture surface 920 is functionalized with the targeted genome manipulating agent 903. In one implementation, a buffer used for this incubation includes a di-cation quencher molecule such as EDTA for preventing cleavage (e.g., Cas9 cleavage). A nonlimiting example of such a buffer contains between 1 mM to 500 mM NaCl, 0 mM to 100 mM HEPES, and 100 mM to 1M EDTA, with a pH between 5 to 8.5.

In certain implementations, the incubation is performed at room temperature for a period ranging from 1 min to 24 hours. The method 900 continues and includes, capturing 904 during incubation, DNA or chromatin genomic fragments containing a target sequence 907 recognized by the targeted genome manipulating agent 903 which is functionalized to the capture surface 920. The method 900 continues and includes washing 906 the capture surface 920 using a washing buffer to keep the target DNA/chromatin fragments bound to the targeted genome manipulating agent 903 and to wash away any unbounded DNA or chromatin fragments. In various implementations, the washing 906 is performed from one to five times at room temperature.

The method 900 continues and releases 915 to the supernatant, one or more chromatin 918 pieces corresponding to a sequence close to the targeted areas of the genome by applying a buffer containing an amount of Mg2+ or di-cation such as Mn2+, Fe2+, Co2+, Ni2+ or Zn2+ to trigger the Cas9 cleavage. And the method 900 continues and includes retrieving the DNA 909 from the cleaved chromatin 918 to be repaired and A-tailed using any appropriate enzymes mix known in the art.

In some implementations, the method 900 continues and (after purification and quantification) includes ligating 908 the cleaved DNA to adapters 921 using T4 DNA ligase. In various implementations, the method 900 continues and includes amplifying 914 the ligated DNA samples after they are purified. The amplifying 914 may be performed using PCR with universal primers 922, 923 and targeting adapters 921 and 923. In certain implementations, the method 900 continues and includes sequencing 916 the purified amplicons e.g. using next-generation sequencing. In some implementations, the adapters 913 and 921 have the same sequence. In other implementations, the adapters 913, 921 have different sequences.

In one implementation, the adapter 913 is configured to produce an overhanging end in one of its extremities and is modified with a blocking moiety at the other extremity to avoid self-ligation and subsequent ligation when ligated in place with a DNA fragment. In various implementations, the method 900 includes reducing the likelihood of self-ligation of the adapter 913, by configuring the 3' end of a first strand of the adapter 913 to include an overhanging thymine linked to rest of the sequence by a phosphothioate bond with the 5' end of the same strand lacking a phosphate moiety and configuring a second strand of the adapter 913 to have a 5' end that includes a phosphate group, and further configuring the 3' end of the second strand to include a moiety configured to prevent any ligation, such as a, for example, a fluorophore molecule, a click chemistry moiety, or inverted dT (reverse linkage).

Figure 10:
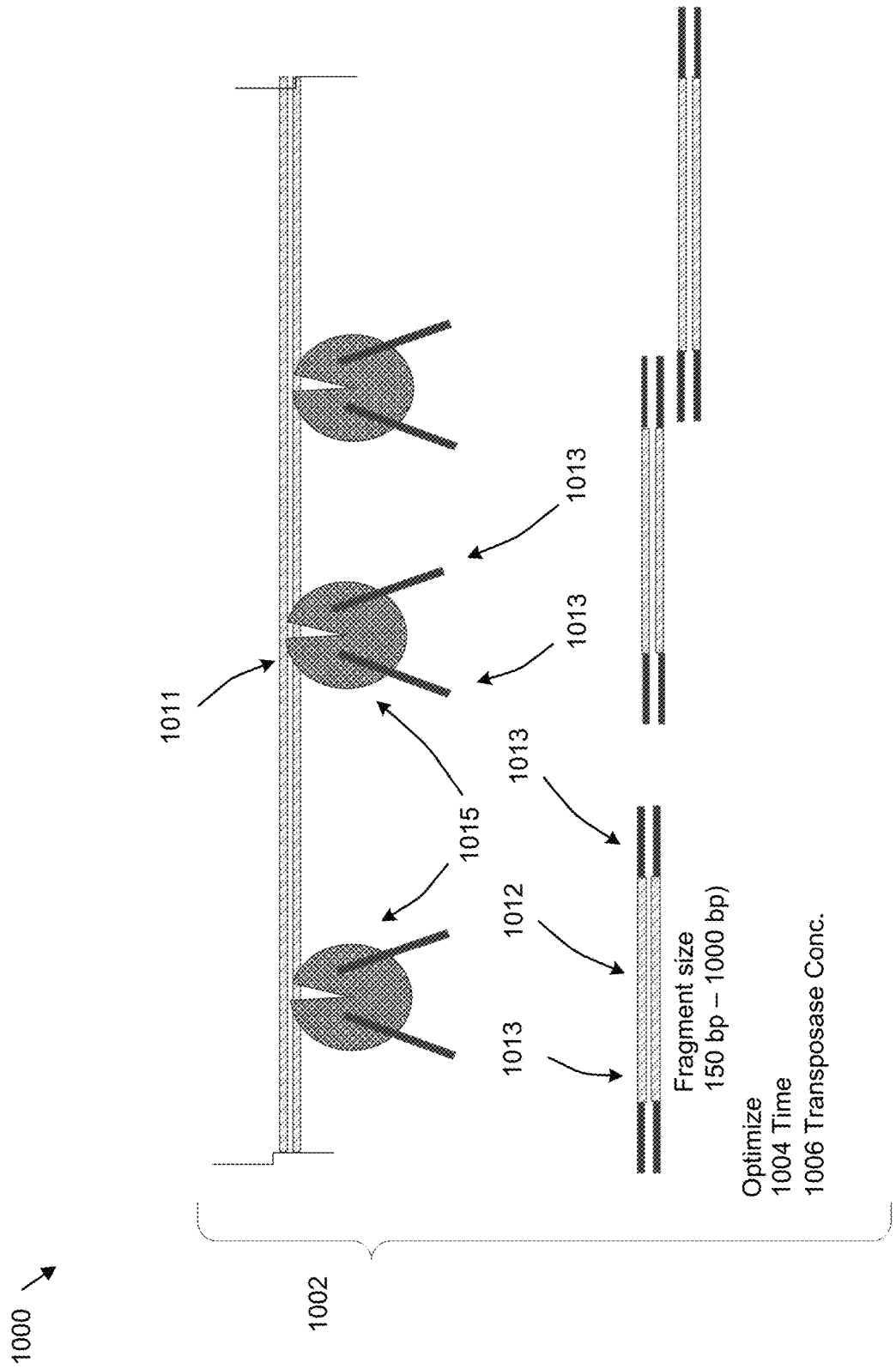
FIG. 10 illustrates tagmentation of a nucleic acid sample for sequencing after measurement of a genome manipulating efficiency parameter, according to one or more examples of the present disclosure.

FIG. 10 illustrates a method 1000 for performing tagging of a nucleic acid sample for sequencing after measurement of a targeted genome manipulating efficiency parameter, according to one or more examples of the present disclosure. In at least one embodiment, the method 1000 begins and includes tagmenting 1002 (e.g., performing one-step tagging and fragmenting) of a nucleic acid sample 1011 (e.g., naked DNA). The tagmenting 1002 uses a transposon 1015 that includes a transposase (e.g., Tn5) and two adapters 1013. The transposon 1015 fragments and transposes the two adapters 1013 into the nucleic acid sample 1011 (e.g., the genomic DNA). In certain implementations, the step of tagmenting 1002 includes optimizing time 1004 and optimizing transposase concentration 1006 to generate one or more tagged fragments 1012 of from about 150 base pairs to about 1000 base pairs.

Figure 11:
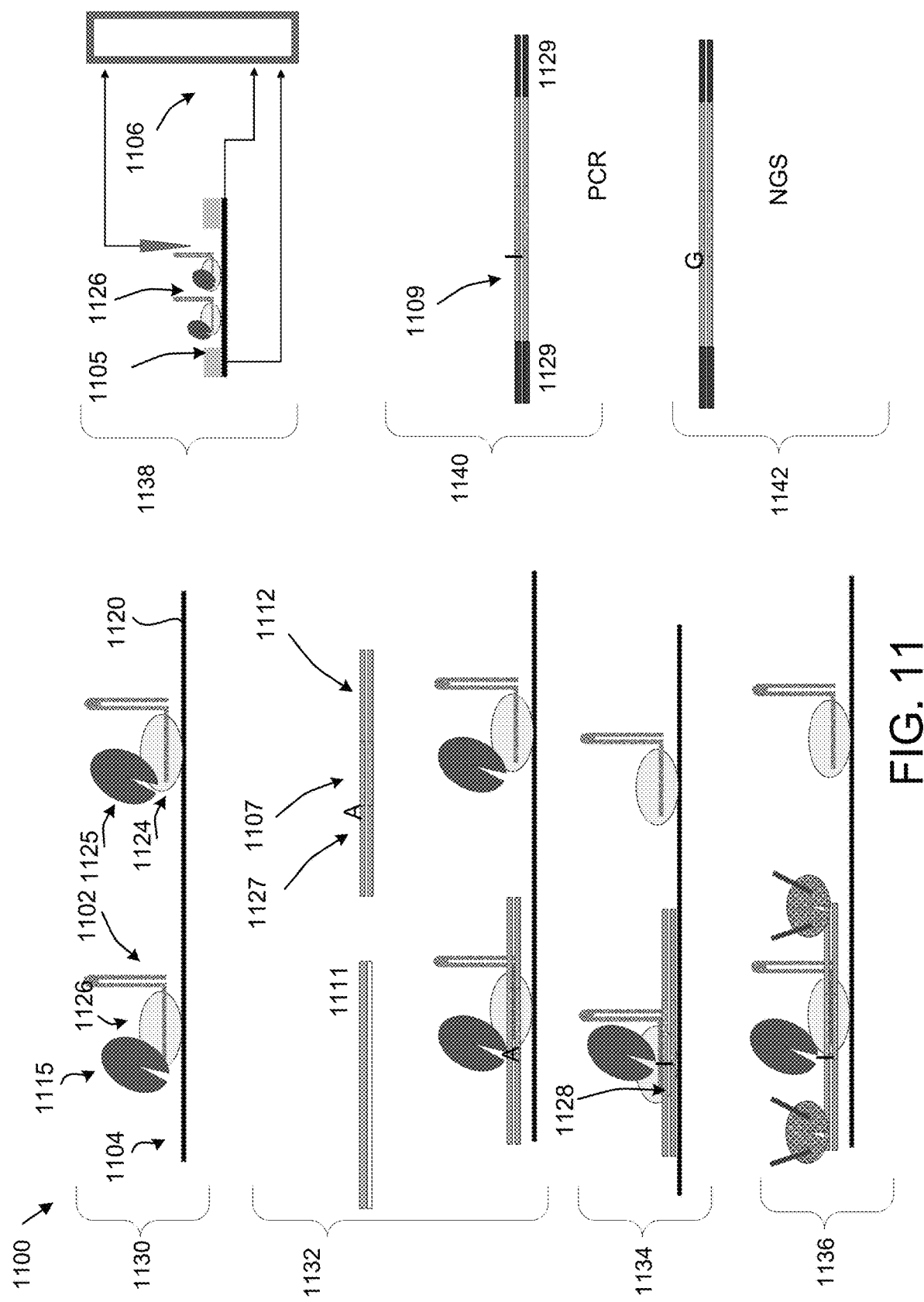
FIG. 11 illustrates using a selected targeted genome manipulating agent for preparing a nucleic acid sample for sequencing, according to one or more examples of the present disclosure.

FIG. 11 illustrates a method 1100 for using a selected targeted genome manipulating agent to prepare a nucleic acid sample 1111 for sequencing, according to one or more examples of the present disclosure. In certain implementations of the systems, apparatuses, and methods disclosed herein, it may be useful to avoid the formation of a double-strand break on a nucleic acid sample e.g., DNA.

Accordingly, in some implementations, the method 1100 begins and includes preparing 1130 chip-based biosensor having a capture surface 1104 functionalized with a targeted genome manipulating agent 1126 that includes a manipulating component 1124 that is non-cleaving. For example, in various implementations, the manipulating component 1124 may be a deactivated Cas protein (also referred to as dCas or dead Cas) which has been mutated in one or both catalytic cutting sites.

In certain implementations, preparing 1130 the functionalized capture surface 1104 with the targeted genome manipulating agent 1126 includes fusing the targeted genome manipulating agent 1126 with a selected enzyme 1125 such as a deaminase, or histone deacetylase, for targeting a specific allele and/or a specific area of the genome to modify a single nucleotide polymorphism ("SNP") and/or to change the methylation of targeted nucleotides of the nucleic acid sample 1111.

In various implementations, the method 1100 includes measuring 1138 one or more chip-based biosensor parameters to assess the binding area of a non-cleaving targeting component of a targeted genome manipulation agent such as dCas9 over the whole genome and to assess one or more adenine base editor off-site targets.

In some implementations, a targeted genome manipulation agent 1126 includes a manipulation component 1124 that is non-cleaving such as an inactive Cas protein. In certain implementations, one nonlimiting example of such a manipulation component 1124 is dCas9. In various implementations, the manipulation component 1124 is combined in fusion with a selected enzyme 1125 (e.g., deaminase) and a targeting component such as gRNA 1102 to form a targeted genome manipulation agent 1126. In various implementations, the capture surface 1120 functionalized with the targeted genome manipulation agent 1126 is a sensing surface of a chip-based biosensor according to one or more aspects of the present disclosure.

In certain implementations, the method 1100 continues and includes fragmenting 1132 the nucleic acid sample 1111 (e.g., genomic DNA) using, by way of nonlimiting example, sonication, acoustic shearing, hydrodynamic shearing and/or endonuclease digestion to produce a nucleic acid sample 1112 that is fragmented (e.g., fragmented DNA). The step of fragmenting 1132 of the method 1100, in certain implementations, further includes incubating the nucleic acid sample 1112 with a functionalized capture surface 1104 of a chip-based biosensor 1105, such as for example the biology gated transistor 402 described above with respect to FIG. 4. In some implementations, the chip-based biosensor 1105 is read by a reader 1106. The method 1100 continues and includes measuring 1138 one or more binding parameters associated with biomolecular binding interactions occurring within a sensing range of a sensing surface of the chip-based biosensor 1105 between the targeted genome manipulation agent 1126 and the fragmented nucleic acid sample 1112.

For certain implementations, such as for example, implementations of chip-based biosensors using field-effect biosensing as described above with respect to FIG. 4, the one or more binding parameters indicating a speed and/or a magnitude of a biochemical and/or biomolecular interaction may include an average change, rate of change, or characteristic shape in any of gate capacitance, a source-drain current, a gate dependent current, and/or a gate voltage. In various implementations, the method includes incubating the functionalized capture surface 1120 (e.g., functionalized with the targeted genome manipulating agent 1126 that is non-cleaving (e.g., dCas complex) with a reference buffer. In some implementations, the method 1100 includes minimizing a Debye layer length of the field-effect biosensor to enhance sensitivity by selecting the reference buffer to have low salt content. In some implementations, the reference buffer includes from 1 mM to 20 mM of NaCl and from 0 mM to 20 mM EDTA In certain implementations, the method 1100 continues and includes as part of the measuring 1138, initially measuring one or more chip-based biosensor parameters such as those listed above in presence of the reference buffer. In some implementations, the method 1100 includes removing the reference buffer and incubating the nucleic acid sample 1112 (e.g., fragmented DNA) resuspended in a binding enhancement buffer configured to enhance the targeting function of the targeted genome manipulation agent 1126 that is non-cleaving (e.g., the dCas9/deaminase/gRNA complex) and to enhance binding of the targeted genome manipulation agent 1126 to a predetermined target sequence 1107. By way of example, the binding enhancement buffer in various implementations includes from 1 mM to 500 mM NaCl, from 0 mM to 100 mM HEPES, from 100 mM to 1M EDTA, and has a pH of between 5 to 8.5.

In various implementations, the method 1100 includes incubating the nucleic acid sample 1112, e.g., the fragmented DNA, in the binding enhancement buffer at room temperature for from about 1 minute to about 16 hours. In certain implementations, after the incubation, the method 1100 includes discarding the supernatant and washing the chip-based biosensor 1105 from 1 to 10 times with a washing buffer. In one example, the washing buffer includes from 1 mM to 500 mM NaCl and from 1 mM to 500 mM EDTA.

In various implementations, the method 1100 includes incubating the chip-based biosensor again with the reference buffer and measuring the parameters again using, for example, the measurement module 124 as described above with respect to FIGS. 1, 2, and/or 4.

In certain implementations, the method 1100 includes determining whether the nucleic acid sample (e.g., the fragmented DNA) includes the targeted SMP 1127 by measuring 1138 biomolecular interactions between the predetermined target sequence 1107 and the selected enzyme 1125 (e.g., deaminase). In some implementations, the measuring 38 includes measuring whether any charged molecules, such as in this example, the nucleic acid sample 1112, induces a change in any of the chip-based biosensor parameters as described above. In various implementations, the method 1100 includes determining an efficiency parameter of the targeted genome manipulating agent 1126 based on comparing differences of intensity between one or more pre-binding incubation parameters recorded before the incubation of the capture surfaces of the chip-based biosensor 1105 with the nucleic acid sample 1112 using, for example, the analysis module 116 described above with respect to FIGS. 1 and 2.

In various implementations, after determining the efficiency parameter of the targeted genome manipulating agent, the method 1100 includes replacing the reference buffer used in performing the measuring with a deamination buffer favoring the deaminase activity of the selected enzyme 1125 (e.g., deaminase) in fusion with the manipulating component 1124 that is non-cleaving (e.g., inactive Cas9).

The method 1100, in certain implementations, includes performing deamination 1134 of an adenine to produce an inosine 1128 that is read as a guanine by a DNA polymerase. In some implementations, the method 1100 includes replacing 1136 the deamination buffer with a solution containing a Tn5 transposase 1115 and two adapters 1129 in a buffer favoring transposition. In various implementations, the adapters 1129 each include a standard universal adapter for NGS. In some implementations, the method 1100 continues and includes amplifying 1140 the deaminated nucleic acid sample 1109 having the adapters 1129 using universal primers 922 and 923 as depicted in step 910 of FIG. 9.

In various implementations, the method 1100 includes capturing portions of the nucleic acid sample comprising on-target and off-target sites that bind to the capture surface of the second chip-based biosensor and releasing the captured sample portions. For example, in certain implementations, the method 1100 continues and includes recovering portions of the captured nucleic acid sample 1109 (e.g., tagged fragmented DNA) from the chip-based biosensor 1105 using a proteinase K digestion to release the captured nucleic acid sample 1109 e.g., tagged and fragmented DNA, into the supernatant. It may be noted that various types of releasing of captured nucleic acid samples may be performed at other points within the method 1100 or within the methods 300, 600, 700, 800, 900, 1000, and/or 1200. The method 1100, in at least one embodiment, includes purifying the amplifying 1140 the released nucleic acid sample 1109, using for example PCR. In some examples, each inosine added by the deaminase is at that point changed to a guanine. In certain implementations, the method continues and includes sequencing 1142 the product of the above steps using NGS.

It may be noted that one or more of the steps of the methods 300, 600, 700, 800, 900, 1000, 1100, and/or 1200, can be performed in part or in whole in any combination with other steps of the aforementioned methods. Similarly, one or more steps of the aforementioned methods may be used in any combination with any components or a whole of the system 100, and/or any of the apparatuses 200, 400, or portions thereof.

Figure 12:
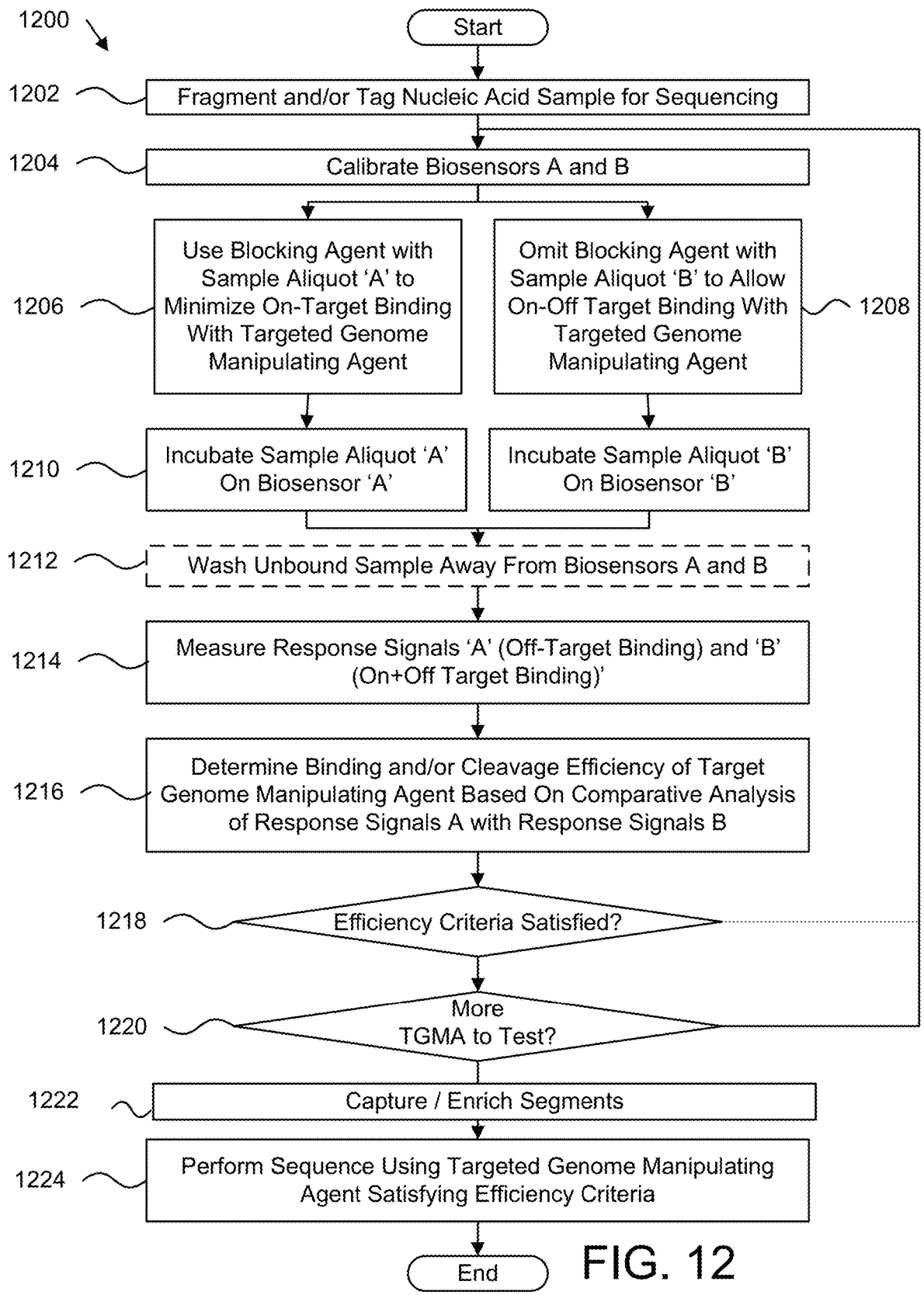
FIG. 12 is a schematic flow chart diagram illustrating a method for enhanced selection of an efficient targeted genome manipulating agent, according to one or more examples of the present disclosure.

FIG. 12 is a schematic flow chart diagram illustrating a method 1200 for enhanced selection of an efficient targeted genome manipulating agent, according to one or more examples of the present disclosure. In one embodiment, the method 1200 begins and includes preparing 1202 a first aliquot and a second aliquot, each aliquot including a nucleic acid sample where the nucleic acid sample is to be measured for detecting biomolecular binding interactions between the nucleic acid sample dispensed to one or more sensing surfaces and a targeted genome manipulating agent that has a genome manipulating component and a targeting component and is functionalized to a capture surface within a sensing range of the one or more sensing surfaces. In some implementations, the targeting component is a guide RNA and the genome manipulating component is a CRISPR-associated protein.

If the intent is to capture sequence for amplification and sequencing based on a positive efficiency determination, the method 1200 may optionally include fragmenting 1202 the nucleic acid sample and tagging the fragments for sequencing prior to determining the efficiency parameters. The fragmenting and tagging can be done separately in certain implementations or in other implementations concurrent fragmenting and tagging are performed for sequencing prior to applying the first and second aliquots respectively to the first and second surfaces.

For repeatability, in various implementations, the method 1200 includes calibrating 1204 each chip-based biosensor to establish a baseline against which to comparatively analyze first and second sets of response signals resulting from binding. This may be especially useful where the first and second sets of response signals during the binding step are relatively weak.

After calibration 1204, the method 1200 continues and includes using 1206 a blocking agent with the first aliquot to minimize on target binding with the targeted genome manipulating agent on the first chip-based biosensor and omitting 1208 a blocking agent in the second aliquot used with the second chip-based biosensor to allow both on-target and off-target binding to occur between the nucleic acid sample and the functionalized capture surface for the second chip-based biosensor. In some implementations, the blocking agent is a deactivated Cas in complex with a blocking RNA configured to bind with a sequence that overlaps the guide sequence of the gRNA. In other implementations, the blocking agent is a synthetic nucleic acid analog configured to bind with the sequence that substantially overlaps the guide sequence of the gRNA.

After incubating 1206 the first aliquot with the blocking agent for sufficiently full-time, the method 1200 continues and includes incubating 1210 the first aliquot which is blocked for on-target binding on the first chip-based biosensor and incubating the second aliquot which is unblocked for both on target and off-target binding.

The method 1200 continues and includes optionally washing 1212 the unbound sample away from the first and second chip-based biosensors. In some implementations, if the measurement bandwidth is sufficiently high and the noise is sufficiently low, the need for the washing step may be reduced.

The method 1200 continues and includes measuring 1214 one or more first and second response signals produced in response to the biomolecular binding interactions occurring between the nucleic acid sample in the first and second aliquots, and the targeted genome manipulating agent on the functionalized capture surfaces of the first and second chip-based biosensors. More than one response signal may be measured using the field-effect biosensor for each chip. For example, response signal for drain current, gate capacitance, gate current, and so forth, may all generate response signals, and may all be monitored for comparison against a second set of response signals from a second chip-based biosensor.

In some implementations, the one or more first and second response signals are optionally measured using a sampling rate that satisfies a predetermined Nyquist criterion for measuring at least one parameter of the biomolecular binding interactions between the nucleic acid sample and the targeted genome manipulating agent over predetermined time period associated with the biomolecular binding interactions.

Measuring using a sampling rate that satisfies a Nyquist criterion for a given parameter allows better insight into the dynamics of that parameter especially where multiple binding interactions are occurring at the same time. The one or more first response signals indicate binding parameters associated with off-target binding between the nucleic acid sample incubated with the blocking agent and the targeted genome manipulating agent functionalized to the capture surfaces within a sensing range of the one or more sensing surfaces of the first chip-based biosensor and the one or more second response signals indicate binding parameters associated with on-target binding plus off-target binding between the nucleic acid sample with the blocking agent omitted and the targeted genome manipulating agent functionalized to the capture surfaces within a sensing range of the one or more sensing surfaces of the second chip-based biosensor.

The method 1200 continues and includes determining 1216 binding efficiency and/or cleavage efficiency of the target genome manipulating agent. For example, in certain implementations based on comparing concentrations derived from the response signals produced by the first chip-based biosensor with concentrations derived from response signals produced by the second chip-based biosensor, with the derivations done using predetermined calibration procedures on representative populations of sample biosensors. Since response signals from both chip-based biosensors include the off-target binding, the difference between the concentrations represents the on-target binding of the targeted genome manipulating agent. At this point, the values for both on target and off-target binding are known and can be compared as a ratio or as a difference.

In certain implementations, the method 1200 continues and includes capturing 1222 from the unblocked second aliquot, portions of the nucleic acid sample comprising on-target and off-target sites that bind to the capture surface of the second chip-based biosensor and releasing the captured sample portions. Thus, the chip-based biosensors may be used for enriching segments performing PCR, etc. In some implementations, the method 1200 continues and includes sequencing 1224 one or more tagged fragments of the target sample in response to determining that the efficiency of the targeted genome manipulating agent satisfies a predetermined efficiency criterion, and the method 1200 ends.

A computer program product comprising a computer readable storage medium having program instructions embodied therewith, the program instructions executable by a processor to cause the processor to control the measurement of one or more first and second response signals produced by a first chip-based biosensor and a second chip-based biosensor, in response to biomolecular binding interactions occurring between a nucleic acid sample and a targeted genome manipulating agent that has an manipulating component and a targeting component and is functionalized to a capture surface within a sensing range of one or more respective sensing surfaces of a first chip-based biosensor and a second chip-based biosensor, wherein the first chip-based biosensor is configured to hold a first aliquot of the nucleic acid sample optionally incubated with a blocking agent configured to bind to a sequence overlapping an on-target sequence of the nucleic acid sample and the second chip-based biosensor is configured to hold a second aliquot of the nucleic acid sample that omits the blocking agent and determine one or more genome manipulating efficiency parameters associated with the targeted genome manipulating agent based on performing a comparative analysis of the first and second response signals.

In certain implementations, the program instructions are executable to cause the processor to perform comparative analyses between genome manipulating efficiency parameters determined using the chip-based biosensors and corresponding genome manipulating efficiency parameters determined using one or more other methods such as the various in silico, in vitro, and in vivo methods described above. For example, after performing fragmenting and adapter ligation in accordance with one or more of the methods 800, 900, 1000, 1100, and 1200, the analysis results of the chip-based biosensors may be comparatively analyzed with one or more of the in vivo, in vitro, and/or in silico binding and/or cleavage efficiency results obtained for the same or similar targeted genome manipulating agent.

Embodiments may be practiced in other specific forms. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An apparatus comprising:
   a first chip-based biosensor and a second chip-based biosensor individually comprising:
     one or more sensing surfaces on channels of liquid gated field effect transistors on a chip, wherein the channels are made of two-dimensional material that extends between a source and a drain of the liquid gated field effect transistors and is selected from graphene and molybdenum disulfide;
     a counter electrode on the chip that is used to incrementally and programmatically adjust a gate voltage of a liquid gate formed over the channels by a sample liquid; and
     a reference electrode on the chip that is used to detect the voltage of the liquid gate formed by the sample liquid;
   wherein the liquid gated field effect transistors to output one or more transistor response signals corresponding to detected biomolecular binding interactions between a nucleic acid sample and one or more capture surfaces functionalized with a targeted genome manipulating agent having a genome manipulating component comprising a CRISPR associated protein Cas molecule (Cas) selected from Cas9, Cas12, and Cas13, and a targeting component comprising a guide RNA (gRNA), wherein the one or more capture surfaces are within a sensing range of the one or more sensing surfaces, and wherein:
     the first chip-based biosensor receives a first aliquot of the nucleic acid sample incubated with a blocking agent selected to bind to a sequence overlapping an on-target sequence of the nucleic acid sample;
     the second chip-based biosensor receives a second aliquot of the nucleic acid sample that omits the blocking agent;
   a measurement controller that measures one or more first and second response signals produced in response to the biomolecular binding interactions occurring between the nucleic acid sample in the first and second aliquots and the targeted genome manipulating agent on the functionalized capture surfaces of first and second chip-based biosensors; and
   an analysis module that determines one or more genome manipulating efficiency parameters associated with the targeted genome manipulating agent based on performing a comparison of the first and second response signals,
   wherein the measurement controller and the analysis module each comprise one or more of hardware circuits, programmable hardware devices, and executable code, the executable code stored on one or more non-transitory computer readable storage media.

2. The apparatus of claim 1, wherein the targeted genome manipulating agent is attached to the one or more capture surfaces via the Cas molecule.

3. The apparatus of claim 1, wherein the targeted genome manipulating agent is attached to the one or more capture surfaces via the gRNA.

4. The apparatus of claim 1, wherein the blocking agent is selected from:
   a deactivated Cas in complex with a blocking RNA configured to bind to a sequence overlapping an on-target sequence of the nucleic acid sample; and
   a synthetic nucleic acid analog configured to bind with the sequence overlapping the on-target sequence of the nucleic acid sample.

5. The apparatus of claim 1, wherein:
   the sensing surfaces corresponding to the first and second chip-based biosensors comprise the one or more capture surfaces; and
   and wherein the first and second chip-based biosensors are configured to detect the biomolecular binding interactions while the nucleic acid sample is in a fluidically undriven state.

6. The apparatus of claim 1, wherein the one or more capture surfaces comprise functionalized magnetic beads configured to be drawn within the sensing range of the sensing surfaces corresponding to the first and second chip-based biosensors.

7. The apparatus of claim 1, wherein the measurement controller is configured to measure the one or more first and second response signals after any unbound components of the first and second aliquots held and incubated respectively on the first and second chip-based biosensors are washed away.

8. The apparatus of claim 7, wherein:
   the one or more first response signals vary in response to changes in binding parameters associated with off-target binding between the nucleic acid sample and the targeted genome manipulating agent; and
   the one or more second response signals vary in response to changes in binding parameters associated with on-target binding plus off-target binding between the nucleic acid sample and the targeted genome manipulating agent.

9. The apparatus of claim 1, wherein:
   instead of the first aliquot being incubated with the blocking agent, both the first aliquot and the second aliquot omit the incubation with the blocking agent;
   the one or more capture surfaces within the sensing range of the sensing surfaces of the first chip-based biosensor are functionalized with a first instantiation of the targeted genome manipulating agent, wherein the genome manipulating component comprises a deactivated Cas selected to not cleave the nucleic acid sample;
   the one or more capture surfaces within the sensing range of the sensing surfaces of the second chip-based biosensor are functionalized with a second instantiation of the targeted genome manipulating agent, wherein the genome manipulating component comprises a Cas selected to cleave the nucleic acid sample; wherein the first and second instantiations of the targeted genome manipulating agent comprise the same gRNA targeting component; and the one or more first and second response signals indicate cleavage parameters associated with binding between the nucleic acid sample and the respective functionalized capture surfaces within a sensing range of the one or more sensing surfaces of the first and second chip-based biosensors.

10. A method comprising:
preparing a first aliquot and a second aliquot individually comprising a nucleic acid sample wherein:
the nucleic acid sample is to be measured utilizing field-effect biosensing for label-free detection of biomolecular binding interactions between the nucleic acid sample dispensed to one or more sensing surfaces and a targeted genome manipulating agent that has a genome manipulating component comprising a CRISPR associated protein Cas molecule (Cas) and a targeting component comprising a guide RNA (gRNA), and is functionalized to capture surfaces of a first chip-based biosensor and a second chip-based biosensor within a sensing range of the one or more sensing surfaces;
the first aliquot is incubated with a blocking agent configured to bind to a sequence that overlaps an on-target sequence of the nucleic acid sample;
the second aliquot omits the blocking agent;
measuring one or more first and second response signals produced in response to the biomolecular binding interactions occurring between the nucleic acid sample in the first and second aliquots, and the targeted genome manipulating agent on the functionalized capture surfaces of the first and second chip-based biosensors; and
determining an efficiency parameter of the targeted genome manipulating agent based on comparatively analyzing the one or more first response signals with the one or more second response signals.

11. The method of claim 10, wherein the blocking agent is selected from:
a deactivated Cas in complex with a blocking RNA configured to bind to a sequence overlapping an on-target sequence of the nucleic acid sample; and
a synthetic nucleic acid analog configured to bind with the sequence that overlaps a guide sequence of the gRNA.

12. The method of claim 10, wherein
the one or more first response signals vary in response to changes in binding parameters associated with off-target binding between the nucleic acid sample incubated with the blocking agent and the targeted genome manipulating agent functionalized to the one or more capture surfaces within a sensing range of the one or more sensing surfaces of the first chip-based biosensor;
the one or more second response signals vary in response to changes in binding parameters associated with on-target binding plus off-target binding between the nucleic acid sample with the blocking agent omitted and the targeted genome manipulating agent functionalized to the one or more capture surfaces within a sensing range of the one or more sensing surfaces of the second chip-based biosensor; and
the one or more first and second response signals are measured using a sampling rate that satisfies a predetermined Nyquist criterion for measuring at least one parameter of the biomolecular binding interactions between the nucleic acid sample and the targeted genome manipulating agent over predetermined time period associated with the biomolecular binding interactions.

13. The method of claim 10, further comprising:
capturing from the second aliquot, portions of the nucleic acid sample comprising on-target and off-target sites that bind to the capture surface of the second chip-based biosensor; and
releasing the captured sample portions.

14. The method of claim 10, further comprising concurrently fragmenting and tagging the nucleic acid sample for sequencing prior to applying the first and second aliquots respectively to the first and second capture surfaces.

15. The method of claim 10, further comprising performing sequencing of one or more tagged fragments of the nucleic acid sample in response to determining that the efficiency parameter of the targeted genome manipulating agent satisfies a predetermined efficiency criterion.

16. A computer program product comprising a non-transitory computer readable storage medium having program instructions embodied therewith, wherein the program instructions are executable by a processor to cause the processor to:
control measurement of one or more first and second response signals produced by a first chip-based biosensor and a second chip-based biosensor individually comprising:
one or more sensing surfaces on channels of liquid gated field effect transistors on a chip, wherein the channels are made of two-dimensional material that extends between a source and a drain of the liquid gated field effect transistors and is selected from graphene and molybdenum disulfide;
a counter electrode on the chip that is configured to incrementally and programmatically adjust a gate voltage of a liquid gate formed over the channels by a sample liquid;
a reference electrode on the chip that is configured to detect the voltage of the liquid gate formed by the sample liquid;
wherein the liquid gated field effect transistors are configured to utilize field-effect biosensing for label-free detection of biomolecular binding interactions occurring between a nucleic acid sample and a targeted genome manipulating agent that has a manipulating component comprising a CRISPR associated protein selected from Cas9, Cas12, and Cas13 and a targeting component comprising a guide RNA) and is functionalized to a capture surface within a sensing range of one or more respective sensing surfaces of a first chip-based biosensor and a second chip-based biosensor, wherein:
the first chip-based biosensor receives a first aliquot of the nucleic acid sample incubated with a blocking agent configured to bind to a sequence overlapping an on-target sequence of the nucleic acid sample; and
the second chip-based biosensor receives a second aliquot of the nucleic acid sample that omits the blocking agent; and
determine one or more genome manipulating efficiency parameters associated with the targeted genome manipulating agent based on performing a comparative analysis of the first and second response signals.

* * * * *